United States Patent
Wong et al.

(10) Patent No.: US 11,591,636 B2
(45) Date of Patent: Feb. 28, 2023

(54) FORCE-CONTROLLED NANOSWITCH ASSAYS FOR SINGLE-MOLECULE DETECTION IN COMPLEX BIOLOGICAL FLUIDS

(71) Applicant: Children's Medical Center Corporation, Boston, MA (US)

(72) Inventors: Wesley Philip Wong, Cambridge, MA (US); Johanna Blass, Saarbruecken (DE); Darren Yang, Somerville, MA (US); Clinton H. Hansen, Cambridge, MA (US)

(73) Assignee: Children's Medical Center Corporation, Boston, MA (US)

( * ) Notice: Subject to any disclaimer, the term of this patent is extended or adjusted under 35 U.S.C. 154(b) by 456 days.

(21) Appl. No.: 16/765,375

(22) PCT Filed: Nov. 20, 2018

(86) PCT No.: PCT/US2018/062141
§ 371 (c)(1),
(2) Date: May 19, 2020

(87) PCT Pub. No.: WO2019/100080
PCT Pub. Date: May 23, 2019

(65) Prior Publication Data
US 2020/0340033 A1    Oct. 29, 2020

Related U.S. Application Data

(60) Provisional application No. 62/588,877, filed on Nov. 20, 2017.

(51) Int. Cl.
*C12Q 1/6804*    (2018.01)

(52) U.S. Cl.
CPC ................ *C12Q 1/6804* (2013.01)

(58) Field of Classification Search
CPC ........ C12Q 1/68; C12Q 1/6804; C07H 21/00; C12P 19/34
See application file for complete search history.

(56) References Cited

U.S. PATENT DOCUMENTS

| | | |
|---|---|---|
| 5,571,677 A | 11/1996 | Gryaznov |
| 5,635,352 A | 6/1997 | Urdea et al. |
| 5,888,731 A | 5/1999 | Yager et al. |
| 5,902,724 A | 5/1999 | Lane et al. |
| 6,143,504 A | 11/2000 | Das et al. |
| 6,232,066 B1 | 5/2001 | Felder et al. |
| 6,251,660 B1 | 6/2001 | Muir et al. |
| 6,569,306 B1 | 5/2003 | Read et al. |
| 6,770,698 B1 | 8/2004 | Chu et al. |
| 8,129,119 B2 | 3/2012 | Jarrell et al. |
| 8,491,454 B2 | 7/2013 | Wong et al. |
| 8,795,143 B2 | 8/2014 | Wong et al. |
| 9,255,905 B1 | 2/2016 | Mellors et al. |
| 9,914,958 B2 | 3/2018 | Wong et al. |
| 9,994,839 B2 | 6/2018 | Lo et al. |
| 2002/0177144 A1 | 11/2002 | Remacle et al. |
| 2002/0182717 A1 | 12/2002 | Karlsson et al. |
| 2003/0143549 A1 | 7/2003 | Yang et al. |
| 2006/0257958 A1 | 11/2006 | Bruno |
| 2007/0026423 A1 | 2/2007 | Koehler et al. |
| 2007/0037152 A1 | 2/2007 | Drmanac |
| 2007/0117109 A1 | 5/2007 | Rothemund |
| 2007/0154899 A1 | 7/2007 | Coull et al. |
| 2007/0155017 A1 | 7/2007 | Wyatt |
| 2008/0038725 A1 | 2/2008 | Luo et al. |
| 2008/0131870 A1 | 6/2008 | Allawi et al. |
| 2008/0312103 A1 | 12/2008 | Nemoto et al. |
| 2009/0087838 A1 | 4/2009 | Reif et al. |
| 2009/0286694 A1 | 11/2009 | Zainiev et al. |
| 2010/0015608 A1 | 1/2010 | Kolpashchikov |
| 2010/0035247 A1 | 2/2010 | Burton |
| 2010/0137120 A1 | 6/2010 | Wong et al. |
| 2010/0206730 A1 | 8/2010 | Hunkapiller et al. |
| 2010/0216658 A1 | 8/2010 | Chaput et al. |
| 2011/0086774 A1 | 4/2011 | Dunaway |
| 2011/0268654 A1 | 11/2011 | Hilderbrand et al. |
| 2012/0058008 A1 | 3/2012 | Corbett et al. |
| 2013/0004523 A1 | 1/2013 | Zubarev et al. |
| 2013/0130884 A1 | 5/2013 | Wong et al. |
| 2013/0196341 A1 | 8/2013 | Neely et al. |
| 2013/0225429 A1 | 8/2013 | Curry |
| 2013/0310260 A1 | 11/2013 | Kim et al. |
| 2013/0344508 A1 | 12/2013 | Schwartz et al. |

(Continued)

FOREIGN PATENT DOCUMENTS

| | | |
|---|---|---|
| JP | H06-508753 A | 10/1994 |
| JP | 2000-312589 A | 8/2000 |

(Continued)

OTHER PUBLICATIONS

International Search Report and Written Opinion dated Feb. 21, 2019 for Application No. PCT/US2018/062141.

(Continued)

*Primary Examiner* — Ethan C Whisenant
(74) *Attorney, Agent, or Firm* — Wolf, Greenfield & Sacks, P.C.

(57) ABSTRACT

Provided herein are methods and products for detecting analytes in a sample. The analytes may be rare analytes such as biomarkers in a biological sample. These methods make use of nucleic acid nanoswitches that adopt a particular conformation and have a particular length in the presence of an analyte.

20 Claims, 15 Drawing Sheets

Specification includes a Sequence Listing.

(56) References Cited

U.S. PATENT DOCUMENTS

| | | |
|---|---|---|
| 2014/0255939 A1 | 9/2014 | Wong et al. |
| 2014/0284213 A1 | 9/2014 | Sabin et al. |
| 2015/0027894 A1 | 1/2015 | Puleo et al. |
| 2015/0099650 A1 | 4/2015 | Sood et al. |
| 2015/0292007 A1 | 10/2015 | Church et al. |
| 2015/0361422 A1 | 12/2015 | Sampson et al. |
| 2017/0369935 A1 | 12/2017 | Koussa et al. |
| 2018/0135043 A1 | 5/2018 | Wong et al. |
| 2018/0223344 A1 | 8/2018 | Chandrasekaran et al. |
| 2018/0291434 A1 | 10/2018 | Wong et al. |
| 2019/0048409 A1 | 2/2019 | Wong et al. |
| 2019/0064056 A1 | 2/2019 | Yang et al. |
| 2019/0070604 A1 | 3/2019 | Wong et al. |
| 2020/0116712 A1 | 4/2020 | Hansen et al. |

FOREIGN PATENT DOCUMENTS

| | | |
|---|---|---|
| JP | 2003-219897 A | 8/2003 |
| JP | 2005-536234 A | 12/2005 |
| JP | 2008-259453 A | 10/2008 |
| JP | 2009-521230 | 6/2009 |
| WO | WO 93/01313 A1 | 1/1993 |
| WO | WO 98/18961 A1 | 5/1998 |
| WO | WO 00/40751 A2 | 7/2000 |
| WO | WO 2004/016767 A2 | 2/2004 |
| WO | WO 2007/076128 A2 | 7/2007 |
| WO | WO 2011/005221 A1 | 1/2011 |
| WO | WO 2011/153211 A1 | 12/2011 |
| WO | WO 2012/058638 A2 | 5/2012 |
| WO | WO 2013/010023 A2 | 1/2013 |
| WO | WO 2014/011800 A1 | 1/2014 |
| WO | WO 2015/006626 A1 | 1/2015 |
| WO | WO 2015/040009 A1 | 3/2015 |
| WO | WO 2015/164602 A2 | 10/2015 |
| WO | WO 2016/089588 A1 | 6/2016 |
| WO | WO 2016/164866 A1 | 10/2016 |
| WO | WO 2017/003950 A2 | 1/2017 |
| WO | WO 2017/147398 A1 | 8/2017 |
| WO | WO 2018/106721 A1 | 6/2018 |

OTHER PUBLICATIONS

International Preliminary Report on Patentability dated Jun. 4, 2020, for Application No. PCT/US2018/062141.
[No Author Listed], Wikipedia Entry, "XhoI." May 14, 2014. Retrieved from the internet. <https://en.wikipedia.org/w/index/php?title=XhoI&oldid=608536958>. Retrieved on Oct. 18, 2016.
Aaij et al., The gel electrophoresis of DNA. Biochim Biophys Acta. May 10, 1972;269(2):192-200.
Baumann et al., Ionic effects on the elasticity of single DNA molecules. Proc Natl Acad Sci U S A. Jun. 10, 1997;94(12):6185-90.
Bellot et al., Recovery of intact DNA nanostructures after agarose gel-based separation. Nat Methods. Mar. 2011;8(3):192-4. doi: 10.1038/nmeth0311-192.
Bishop et al., Electrophoretic separation of viral nucleic acids on polyacrylamide gels. J Mol Biol. Jun. 28, 1967;26(3):373-87.
Bustamante et al., Entropic elasticity of lambda-phage DNA. Science. Sep. 9, 1994;265(5178):1599-600.
Bustamante et al.,Ten years of tension: single-molecule DNA mechanics. Nature. Jan. 23, 2003;421(6921):423-7.
Butko et al., Detection of Ligand-Induced Conformational Changes in Oligonucleotides by Second-Harmonic Generation at a Supported Lipid Bilayer Interface. Anal Chem. Nov. 1, 2016;88(21):10482-10489. Epub Oct. 12, 2016. Accepted Manuscript, 23 pages.
Chandrasekaran et al., Label-free Detection of Specific Nucleic Acid Sequences using DNA Nanoswitches. The RNA Institute, University at Albany, State University of New York.
Chandrasekaran et al., Programmable DNA Nanoswitches for Detection of Nucleic Acid Sequences. ACS Sens., 2016, 1 (2), pp. 120-123.

Cheng et al., Early pregnancy factor in cervical mucus of pregnant women. Am J Reprod Immunol. Feb. 2004;51(2):102-5.
Chilkoti et al., Molecular Origins of the Slow Streptavidin-Biotin Dissociation Kinetics. J Am Chem Soc. 1995; 117(43):10622-8.
Chivers et al., A streptavidin variant with slower biotin dissociation and increased mechanostability. Nat Methods. May 2010;7(5):391-3. doi: 10.1038/nmeth.1450. Epub Apr. 11, 2010.
Cho et al., A genomic-scale view of the cAMP response element-enhancer decoy: a tumor target-based genetic tool. Proc Natl Acad Sci U S A. Nov. 26, 2002;99(24):15626-31. Epub Nov. 18, 2002.
Conde et al., Implantable hydrogel embedded dark-gold nanoswitch as a theranostic probe to sense and overcome cancer multidrug resistance. Proc Natl Acad Sci U S A. Mar. 17, 2015;112(11):E1278-87. doi: 10.1073/pnas.1421229112. Epub Mar. 2, 2015.
Deniz et al., Single-molecule biophysics: at the interface of biology, physics and chemistry. J R Soc Interface. Jan. 6, 2008;5(18):15-45.
Devaraj et al., Biomedical applications of tetrazine cycloadditions. Acc Chem Res. Sep. 20, 2011;44(9):816-27. doi: 10.1021/ar200037t. Epub May 31, 2011.
Doshi et al., In vitro nanobody discovery for integral membrane protein targets. Sci Rep. Oct. 24, 2014;4:6760. doi: 10.1038/srep06760.
Douglas et al., A logic-gated nanorobot for targeted transport of molecular payloads. Science. Feb. 17, 2012;335(6070):831-4. doi: 10.1126/science.1214081.
Douglas et al., Self-assembly of DNA into nanoscale three-dimensional shapes. Nature. May 21, 2009;459(7245):414-8. doi: 10.1038/nature08016.
Evans et al., Dynamic strength of molecular adhesion bonds. Biophys J. Apr. 1997;72(4):1541-55.
Evans et al., Forces and bond dynamics in cell adhesion. Science. May 25, 2007;316(5828):1148-53.
Evans, Probing the relation between force—lifetime—and chemistry in single molecular bonds. Annu Rev Biophys Biomol Struct. 2001;30:105-28.
Fazio et al., DNA curtains and nanoscale curtain rods: high-throughput tools for single molecule imaging. Langmuir. Sep. 16, 2008;24(18):10524-31. doi: 10.1021/la801762h. Epub Aug. 7, 2008.
França et al., A review of DNA sequencing techniques. Q Rev Biophys. May 2002;35(2):169-200.
Green, Avidin and streptavidin. Methods Enzymol. 1990;184:51-67.
Greenleaf et al., High-resolution, single-molecule measurements of biomolecular motion. Annu Rev Biophys Biomol Struct. 2007;36:171-90.
Halvorsen et al., Binary DNA nanostructures for data encryption. PLoS One. 2012;7(9):e44212. doi: 10.1371/journal.pone.0044212. Epub Sep. 11, 2012.
Halvorsen et al., Cross-platform comparison of nucleic acid hybridization: toward quantitative reference standards. Anal Biochem. Nov. 15, 2014;465:127-33. doi: 10.1016/j.ab.2014.08.001. Epub Aug. 12, 2014.
Halvorsen et al., Massively Parallel Single-Molecule Manipulation Using Centrifugal Force. Biophys J. Jun. 2, 2010;98(11):L53-5.
Halvorsen et al., Nanoengineering a single-molecule mechanical switch using DNA self-assembly. Nanotechnology. Dec. 9, 2011;22(49):494005. doi: 10.1088/0957-4484/22/49/494005. Epub Nov. 21, 2011.
Halvorsen, Probing Weak Single-Molecule Interactions: Development and Demonstration of a New Instrument. Boston University, College of Engineering dissertation. 2007: 102 pages.
Hanke et al., Entropy loss in long-distance DNA looping. Biophys J. Jul. 2003;85(1):167-73.
Hansen et al., Nanoswitch-linked immunosorbent assay (NLISA) for fast, sensitive, and specific protein detection. PNAS. Sep. 26, 2017;114(39):10367-10372. Supporting Information, 4 pages.
Hassur et al., UV shadowing—a new and convenient method for the location of ultraviolet-absorbing species in polyacrylamide gels. Anal Biochem. May 1974;59(1):162-4.
Hellman et al., Electrophoretic mobility shift assay (EMSA) for detecting protein-nucleic acid interactions. Nat Protoc. 2007;2(8):1849-61.

(56) References Cited

OTHER PUBLICATIONS

Hopwood et al., Integrated microfluidic system for rapid forensic DNA analysis: sample collection to DNA profile. Anal Chem. Aug. 15, 2010;82(16):6991-9. doi: 10.1021/ac101355r.

Idili et al., Programmable pH-triggered DNA nanoswitches. J Am Chem Soc. Apr. 23, 2014;136(16):5836-9. doi: 10.1021/ja500619w. Epub Apr. 9, 2014. Abstract only.

Jones et al., Nanomaterials. Programmable materials and the nature of the DNA bond. Science. Feb. 20, 2015;347(6224):1260901. doi: 10.1126/science.1260901.

Jung et al., Binding and Dissociation Kinetics of Wild-Type and Mutant Streptavidins on Mixed Biotin-Containing Alkylthiolate Monolayers. Langmuir. Nov. 28, 2000;16(24): 9421-32.

Khalil et al., Single M13 bacteriophage tethering and stretching. Proc Natl Acad Sci U S A. Mar. 20, 2007;104(12):4892-7. Epub Mar. 13, 2007.

Kim et al., A mechanically stabilized receptor-ligand flex-bond important in the vasculature. Nature. Aug. 19, 2010;466(7309):992-5. doi: 10.1038/nature09295.

Kim et al., Multiplexed single-molecule assay for enzymatic activity on flow-stretched DNA. Nat Methods. May 2007;4(5):397-9. Epub Apr. 15, 2007.

Kleiner et al., Small-molecule discovery from DNA-encoded chemical libraries. Chem Soc Rev. Dec. 2011;40(12):5707-17. doi: 10.1039/c1cs15076f. Epub Jun. 14, 2011.

Klumb et al., Energetic roles of hydrogen bonds at the ureido oxygen binding pocket in the streptavidin-biotin complex. Biochemistry. May 26, 1998;37(21):7657-63.

Koch et al., Prospects and limitations of the rosette inhibition test to detect activity of early pregnancy factor in the pig. J Reprod Fertil. May 1985;74(1):29-38.

Koussa et al., DNA nanoswitches: a quantitative platform for gel-based biomolecular interaction analysis. Nat Methods. Feb. 2015; 12(2):123-6. doi: 10.1038/nmeth.3209. Epub Dec. 8, 2014.

Koussa et al., Protocol for sortase-mediated construction of DNA-protein hybrids and functional nanostructures. Methods. May 15, 2014;67(2):134-41. doi: 10.1016/j.ymeth.2014.02.020. Epub Feb. 22, 2014.

Kufer et al., Single-molecule cut-and-paste surface assembly. Science. Feb. 1, 2008;319(5863):594-6. doi: 10.1126/science.1151424.

Leier et al., Cryptography with DNA binary strands. Biosystems. Jun. 2000;57(1):13-22.

McDonell et al., Analysis of restriction fragments of T7 DNA and determination of molecular weights by electrophoresis in neutral and alkaline gels. J Mol Biol. Feb. 15, 1977; 110(1):119-46.

Modi et al., A DNA nanomachine that maps spatial and temporal pH changes inside living cells. Nat Nanotechnol. May 2009;4(5):325-30. doi: 10.1038/nnano.2009.83. Epub Apr. 6, 2009. Abstract only.

Morton et al., Early pregnancy factor. Semin Reprod Endocrinol. May 1992;10:72-82.

Morton et al., Rosette inhibition test: A multicentre investigation of early pregnancy factor in humans. J Reprod Immunol. Sep. 1982;4(5):251-61.

Nelson et al., Tethered particle motion as a diagnostic of DNA tether length. J Phys Chem B. Aug. 31, 2006;110(34):17260-7. Abstract only.

Neuman et al., Single-molecule force spectroscopy: optical tweezers, magnetic tweezers and atomic force microscopy. Nat Methods. Jun. 2008;5(6):491-505. doi: 10.1038/nmeth.1218.

Park et al., Dual blockade of cyclic AMP response element—(CRE) and AP-1-directed transcription by CRE-transcription factor decoy oligonucleotide, gene-specific inhibition of tumor growth. J Biol Chem. Jan. 15, 1999;274(3):1573-80.

Pei et al., A DNA nanostructure-based biomolecular probe carrier platform for electrochemical biosensing. Adv Mater. Nov. 9, 2010;22(42):4754-8. doi: 10.1002/adma.201002767.

Quek et al., Mechanically controlled binary conductance switching of a single-molecule junction. Nat Nanotechnol. Apr. 2009;4(4):230-4. doi:10.1038/nnano.2009.10. Epub Mar. 1, 2009.

Rief et al., Sequence-dependent mechanics of single DNA molecules. Nat Struct Biol. Apr. 1999;6(4):346-9.

Ritort, Single-molecule experiments in biological physics: methods and applications. J Phys Condens Matter. Aug. 16, 2006;18(32):R531-83. doi:10.1088/0953-8984/18/32/R01. Epub Jul. 25, 2006.

Rothemund, Folding DNA to create nanoscale shapes and patterns. Nature. Mar. 16, 2006;440(7082):297-302.

Sacca et al., DNA origami: the art of folding DNA. Angew Chem Int Ed Engl. Jan. 2, 2012;51(1):58-66. doi: 10.1002/anie. 201105846. Epub Dec. 7, 2011.

Seeman, DNA in a material world. Nature. Jan. 23, 2003;421(6921):427-31.

Seeman, Nanomaterials based on DNA. Annu Rev Biochem. 2010;79:65-87. doi: 10.1146/annurev-biochem-060308-102244.

Shroff et al., Biocompatible force sensor with optical readout and dimensions of 6 nm3. Nano Lett. Jul. 2005;5(7):1509-14.

Shroff et al., Optical measurement of mechanical forces inside short DNA loops. Biophys J. Mar. 15, 2008;94(6):2179-86. Epub Dec. 7, 2007.

Smith et al., Overstretching B-DNA: the elastic response of individual double-stranded and single-stranded DNA molecules. Science. Feb. 9, 1996;271(5250):795-9.

Strunz et al., Dynamic force spectroscopy of single DNA molecules. Proc Natl Acad Sci U S A. Sep. 28, 1999;96(20):11277-82.

Su et al., Nucleic acid fluorescent probes for biological sensing. Appl Spectrosc. Nov. 2012;66(11):1249-62. doi: 10.1366/12-06803. Review.

Svoboda et al., Direct observation of kinesin stepping by optical trapping interferometry. Nature. Oct. 21, 1993;365(6448):721-7.

Thorne, Electrophoretic separation of polyoma virus DNA from host cell DNA. Virology. Jun. 1966;29(2):234-9.

Thuring et al., A freeze-squeeze method for recovering long DNA from agarose gels. Anal Biochem. May 26, 1975;66(1):213-20.

Wiita et al., Force-dependent chemical kinetics of disulfide bond reduction observed with single-molecule techniques. Proc Natl Acad Sci U S A. May 9, 2006;103(19):7222-7. Epub Apr. 27, 2006.

Williams et al., Entropy and heat capacity of DNA melting from temperature dependence of single molecule stretching. Biophys J. Apr. 2001;80(4):1932-9.

Winfree et al., Design and self-assembly of two-dimensional DNA crystals. Nature. Aug. 6, 1998;394(6693):539-44.

Wong et al., The effect of integration time on fluctuation measurements: calibrating an optical trap in the presence of motion blur. Opt Express. Dec. 11, 2006;14(25):12517-31.

Yang et al., An integratable microfluidic cartridge for forensic swab samples lysis. Forensic Sci Int Genet. Jan. 2014;8(1):147-58. doi: 10.1016/j.fsigen.2013.08.012. Epub Sep. 8, 2013.

Yang et al., Multiplexed single-molecule force spectroscopy using a centrifuge. Nat Commun. Mar. 17, 2016;7:11026(1-7). doi: 10.1038/ncomms11026. PubMed PMID: 26984516; PubMed Central PMCID: PMC4800429.

Zadeh et al., NUPACK: Analysis and design of nucleic acid systems. J Comput Chem. Jan. 15, 2011;32(1):170-3. doi: 10.1002/jcc.21596.

Zhang et al., Mechanoenzymatic cleavage of the ultralarge vascular protein, von Willebrand Factor. Science. Jun. 5, 2009;324(5932):1330-4.

Zheng et al., From molecular to macroscopic via the rational design of a self-assembled 3D DNA crystal. Nature. Sep. 3, 2009;461(7260):74-7. doi: 10.1038/nature08274.

U.S. Appl. No. 14/356,282, filed May 5, 2014, Granted, U.S. Pat. No. 9,914,958.

U.S. Appl. No. 15/888,941, filed Feb. 5, 2018, Published, 2018-0291434.

U.S. Appl. No. 15/578,962, filed Dec. 1, 2017, Published, 2018-135043.

U.S. Appl. No. 15/738,982, filed Dec. 21, 2017, Published, 2018-0223344.

U.S. Appl. No. 15/533,473, filed Jun. 6, 2017, Published, 2014-0369935.

U.S. Appl. No. 16/074,952, filed Aug. 2, 2018, Published, 2019-0048409.

(56) References Cited

OTHER PUBLICATIONS

U.S. Appl. No. 16/087,500, filed Sep. 21, 2018, Published, 2019-0070604.
U.S. Appl. No. 16/088,006, filed Sep. 24, 2018, Published, 2020-0116712.
PCT/US2018/062141, Feb. 21, 2019, International Search Report and Written Opinion.
PCT/US2018/062141, Jun. 4, 2020, International Preliminary Report on Patentability.

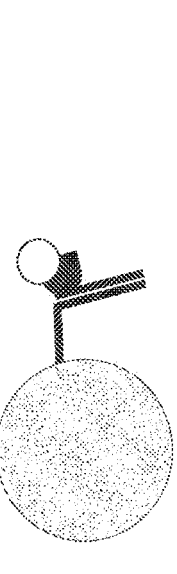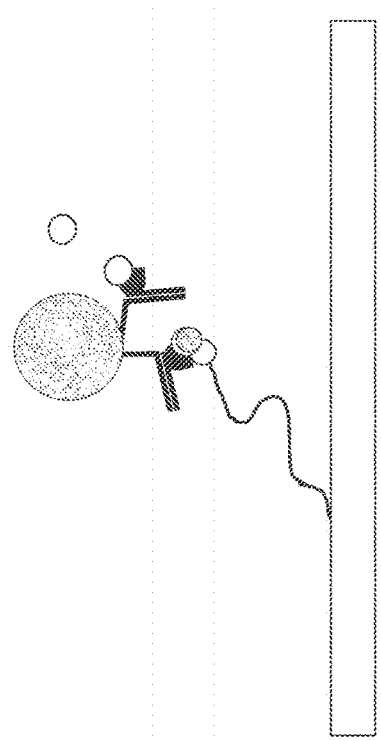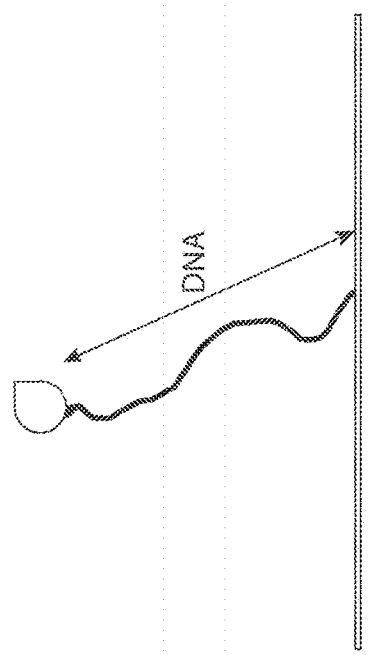
FIG. 1G
FIG. 1H
FIG. 1I

SEQUENCE LISTING

<160> NUMBER OF SEQ ID NOS: 1

<210> SEQ ID NO 1
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 1 tctataactaactcccaaactataaactc                                  29

FORCE-CONTROLLED NANOSWITCH ASSAYS FOR SINGLE-MOLECULE DETECTION IN COMPLEX BIOLOGICAL FLUIDS

RELATED APPLICATIONS

This application is a National Stage Filing under 35 U.S.C. § 371 of International Application No. PCT/US2018/062141, filed Nov. 20, 2018, which claims the benefit under 35 U.S.C. § 119(e) of U.S. Provisional Application Ser. No. 62/588,877, entitled "FORCE-CONTROLLED NANOSWITCH ASSAYS FOR SINGLE-MOLECULE DETECTION IN COMPLEX BIOLOGICAL FLUIDS", filed on Nov. 20, 2017, the entire contents of each of which are incorporated by reference herein.

FEDERALLY SPONSORED RESEARCH

This invention was made with government support under Grant number CA212827 awarded by The National Institutes of Health. The government has certain rights in the invention.

BACKGROUND OF INVENTION

Many advances in research, clinical practice and biosecurity depend on the ability to detect and quantify molecules in biological samples. While numerous detection techniques exist, they suffer trade-offs between speed, sensitivity, and ease of use. The demand for an accessible platform with a fast and sensitive detection capability is ever increasing, especially for proteins, for which the most accurate tests require large, expensive laboratory instruments.

The recent outbreaks of infectious diseases, such as Zika and Ebola, demonstrate the need for sensitive protein detection techniques that can be performed in non-laboratory settings. While small amounts of infectious agents can be identified through genetic materials such as DNA or RNA, nucleic-acid based detection requires a polymerase chain reaction (PCR) step to amplify the gene of interest. PCR can be time-consuming and requires specialized instrumentation, which creates a significant hurdle to bringing genetic-based detections outside the laboratory into settings where they are needed. An alternative approach is to detect the proteins related to the infectious agents. However, insufficient sensitivity of most point-of-care and even laboratory assays prevents detection of proteins present at low concentrations during the early stages of an infection.

The current gold-standard method for protein detection is enzyme-linked immunosorbent assay (ELISA) which was introduced nearly five decades ago. One common variant called sandwich-ELISA was developed to have high-specificity when analyzing complex biological fluid. The sandwich-ELISA uses two antibodies to detect the protein analyte by binding to two different regions (epitopes). The sensitivity limit of ELISAs often just reaches the picomolar (pM, 10-12 M) range which is insufficient for many applications.

Mechano(bio)chemical sensing is a central concept for biological systems to sense and respond to their environment [1, 2]. A force signal is transduced into a biochemical response or vice versa, often based on conformational changes of the involved molecules. The mechanical changes can be monitored using single-molecule techniques [1]. The potential for single-molecule resolution and the high selectivity of biochemical sensing makes them interesting for medical detection applications [3]. While AFM, optical or magnetic tweezers and other standard single-molecule techniques were successful in monitoring the change in mechanical properties of a single molecule, they suffer from low throughput and unspecific adhesive forces [4]. Moreover, the distinction between single and multiple interactions as well as gaining sufficient statistics is a challenge when using standard single-molecule methods.

Recently, DNA constructs were shown to multiply the number of available probes in optical tweezer experiments enabling the detection of biologically relevant biomarker concentrations at picomolar levels [3]. Additional studies in solution demonstrated DNA origami constructs as promising approach for ultra-sensitive detection caused by their fast reaction kinetics in solution [5]. However, purely solution-based methods often lack a way to distinguish between specific and nonspecific adhesive forces leading to high false positive rates or significant cross-reactivity. Using these methods, detection in complex bodily fluids such as serum or whole blood will be very challenging due to the large variety of proteins species and their potential nonspecific adhesion.

SUMMARY OF INVENTION

This disclosure provides, inter alia, a novel single-molecule detection technique for analytes such as but not limited to biomarkers including cancer biomarkers. Such markers may be present and thus provided in complex bodily fluids. The methods provided herein have been demonstrated to detect such analytes with attomolar sensitivity. The technique is based on nucleic acid, e.g., DNA, constructs, referred to herein as nanoswitches, attached to a solid surface, such as a wall of a microfluidic channel. The nanoswitches undergo a conformation change upon binding to a specific analyte. This conformational change can be efficiently read-out by parallel stretching of thousands of surface-tethered nanoswitches under force, such as hydrodynamic flow. Mechanical proofreading may be used to distinguish between specific and non-specific binding. The force-controlled read-out enables low background detection with a nominal limit of detection of 0.4 aM for DNA in buffer, much lower than conventional ELISA assays, or previous mechanosensing techniques. The approach is demonstrated by detection of prostate specific antigen (PSA) in a complex biological sample (e.g., a serum sample) at a limit of detection of 117 aM. By using massive parallel dynamic force spectroscopy performed with the same setup, an LOD of PSA detection in whole blood of 13 fM was achieved.

Unlike methods of the prior art, this method observes single nanoswitches and measures a read-out, such as nanoswitch length or rupture force, from individual nanoswitches, rather than observing and measuring a read-out from a population of nanoswitches (e.g., as may occur in a gel electrophoresis based method). It is to be understood that the methods provided herein do not use gel electrophoresis and thus they may be referred to as non-electrophoretic methods. Instead nanoswitches are immobilized either on a surface, through for example a covalent or non-covalent linkage, or they may be inserted in a lipid bilayer and immobilized at a barrier.

Certain methods provided herein are methods for detecting an analyte in a sample, and these methods generally comprise
(a) contacting a sample with a plurality of nanoswitches for a time and under conditions sufficient for binding of an analyte to its respective nanoswitch(es) in the plurality, thereby generating closed nanoswitches, (b) tethering the closed nanoswitches to a surface, and (c) measuring length of a single surface-tethered closed nanoswitch and/or detecting a rupture event in a single surface-tethered closed nanoswitch, under force.

Certain methods provided herein may comprise, between steps (a) and (b) above, a further step of (a') enriching and isolating closed nanoswitches each bound to its respective analyte.

This step may be included in the method to improve limit of detection (LOD), particularly when the analyte being detected is known to be or is suspected to be at a very low concentration (e.g., at the attomolar range or lower).

The nanoswitch is a nucleic acid conjugated to a first and a second analyte-binding agent (referred to interchangeably herein as an analyte-binding probe). When both the first and second agents are bound to the same analyte, the nanoswitch adopts a looped conformation and has a shorter length as compared to the length of the nanoswitch when it is not bound to the analyte.

Upon contacting the sample with the plurality of nanoswitches, particularly in the presence of an analyte, a mixture of open and closed nanoswitches will be formed. The ratio of open to closed nanoswitches will vary depending on the ratio of nanoswitch concentration and analyte concentration.

In some embodiments, the analyte is present in the sample at a concentration ranging from about 10 attomolar to about 10 femtomolar. In some embodiments, the analyte is present in the sample at a concentration ranging from about 10 femtomolar to about 100 picomolar.

In some embodiments, the nanoswitches are present at a concentration that is $10^3$ to $10^5$ greater than analyte concentration. In some embodiments, the nanoswitches are present in a concentration ranging from about 150 picomolar to about 1.5 nanomolar.

In some embodiments, the nanoswitch (which may be referred to herein as a tether) is first attached to a particle such as a bead, which is then attached to a surface, though the nanoswitch or tether can first be attached to a surface, which can then be attached to a particle.

It is to be understood that any aspect or embodiment described herein that refers to a particle is intended and should be understood to refer and relate equally to a bead. Such beads may be magnetic beads or non-magnetic beads and may further be fluorescent beads or non-fluorescent beads. Every combination of bead types is contemplated and embraced by this disclosure. Thus, in some instances, the description provided herein refers interchangeably to a particle and a bead.

In some embodiments, the method measures length of the surface-tethered closed nanoswitch. In other embodiments, the method measures the presence or absence of tethered beads through direct visualization or through the Brownian motion of the beads.

As used herein, the length of a nanoswitch is defined as the distance from one end of the nanoswitch to the other end of the nanoswitch. This is typically measured while the nanoswitch is extended (or stretched out), for example under hydrodynamic force. To illustrate, a nanoswitch having a looped conformation, as shown in FIG. 1B, has a shorter length as compared to the nanoswitch in the linear conformation, as shown in FIG. 1B. That is, when stretched out, the end to end distance of the two conformations is different with the looped conformation having a shorter length. The end-to-end distance may also be represented as the distance between the surface anchors such as the particle or bead on one end and a surface on the other end. The skilled person will appreciate that the contour length of the chain segments experiencing tension between the two surface attachment points is shorter when the nanoswitch is in the looped (or closed) conformation compared to the unlooped (or open) conformation.

In some embodiments, the length of the surface-tethered closed nanoswitch is measured under constant force. Constant force, as used herein, means that a force is applied to the nanoswitch and its length measured at that force. The force that is used may vary between different nanoswitches, and may depend on the nature and binding strengths of the analyte-binding agents that are conjugated to the nanoswitch.

Thus, in some embodiments, the force is a constant force. The constant force may be in the range of about 4 pN to about 8 pN, in some instances.

In some embodiments, the force is a dynamic force. The dynamic force may be a force that increases from zero to about 16 pN.

In some embodiments, the force is hydrodynamic force. In other embodiments, the force is magnetic force or centrifugal force.

In some embodiments, the force is applied in the plane parallel or almost parallel to the surface, such as with hydrodynamic force and the nanoswitch length can be measured by altering the direction of the force, such as by reversing the flow. In other embodiments, the force is applied close to perpendicularly or at an angle from the surface, such as with magnetic force or centrifugal force, and the nanoswitch length can be measured by the distance of the bead to the surface.

In some embodiments, the method detects a rupture event in the surface-tethered closed nanoswitch. In some embodiments, the rupture event is detected under dynamic force. In still other embodiments, the rupture event is detected under constant force. In these latter instances, the lifetime of the closed nanoswitch is measured as a function of force.

A rupture event, as used herein, means the dissociation of the bond between the analyte and one of the analyte-binding agents. Typically, the rupture event is the dissociation of the bond between the analyte and the more weakly binding analyte-binding agent (e.g., the agent having the lower affinity for the analyte). Once such bond ruptures, the nanoswitch no longer has a looped conformation. It is to be understood, however, that the analyte usually remains bound to the nanoswitch through the other analyte-binding agent (the one having a higher binding strength, or higher affinity for the analyte). In the rupture event measurements, it is possible to measure a plurality of rupture events by subjecting the nanoswitch to increasing force until a rupture event is detected, and then reducing force thereby allowing the re-association of the ruptured bond, and repeating these steps a number of time. The rupture event is detected by a change in the length of the nanoswitch, from that of a closed conformation to that of an open conformation (i.e., detecting an increase in the length). The readout is the force at which the rupture event occurs under dynamic force application (or the lifetime of the bond or closed nanoswitch under constant force application of), as this will be dictated by the particular analyte-binding agent and analyte. This analysis may further take advantage of the fact the nanoswitch may undergo conversion from the open to the closed conformations in order to perform the same analysis repeatedly, thereby obtaining a more exact measure of the rupture force.

It will be further understood based on the foregoing that it may be preferable in some instances to conjugate analyte-binding agents of differing binding strengths (or affinities) to the nanoswitch.

Thus, in some embodiments, the method detects a plurality of rupture events in the same surface-tethered closed nanoswitch under dynamic force, and the method then identifies the force at which the maximum number of rupture events occurs.

In some embodiments, closed nanoswitches may be physically separated from open nanoswitches, and thereby enriched. This may be accomplished using gel electrophoresis since the closed nanoswitches migrate more slowly in a gel as compared to the open nanoswitches. Similar enrichment procedures may be used in other aspects and embodiments described herein.

In some embodiments, the closed nanoswitches are enriched and isolated by (i) cleaving open and closed nanoswitches present after (a) with one or more endonucleases between the first and second analyte-binding agents, or by other means including chemical means or biomolecular means, (ii) end-conjugating the cleaved nanoswitches with a particle, (iii) isolating the particle-conjugated nanoswitches, and (iv) binding the particle-conjugated nanoswitches to a surface.

In some embodiments, the nanoswitches are provided in a form that is already end-conjugated with a particle. In some embodiments, the method first end-conjugates the nanoswitches to a particle. It is to be understood that this intends that every nanoswitch is end-conjugated to a different particle.

In some embodiments, the one or more endonucleases is two endonucleases. The endonucleases may be restriction endonucleases (e.g., sequence-specific endonucleases). They will be selected based on the sequence of the nanoswitch and/or the sequence of the nanoswitch will be designed to be cleaved by one or two endonucleases at particular locations. In some embodiments, the endonucleases are AfeI and AlwI.

In some embodiments, other means of cleaving open and closed nanoswitches include the use of toehold-mediated strand displacement to remove an oligonucleotide that is bridging a nick (which could be introduced into the scaffold using a nicking restriction enzyme), or using a reducing agent to break one or more disulfide bonds that are holding the nanoswitch together.

In some embodiments, the particle is a weight-bearing particle. In some embodiments, the particle is a detectable particle. An example of this latter particle is a fluorescent particle such as a quantum dot. In some embodiments, the particle facilitates the physical separation of certain nanoswitches from other nanoswitches. An example of this latter particle is a magnetic particle.

In some embodiments, the nanoswitch is labeled with detectable stain or dye.

In some embodiments, the analyte-binding agents are antibodies or antigen-binding antibody fragments. In some embodiments, the analyte-binding agents on a nanoswitch will differ from each other in terms of their binding strengths or affinities for the analyte and/or the particular epitopes to which they bind. Typically, the analyte-binding agents will bind to different epitopes on the same analyte, and at different binding strengths. Thus, in some embodiments, the nanoswitch is a partially double-stranded nucleic acid comprising a first analyte-binding agent at a first location and a second analyte-binding agent at a second location, and first and second analyte-binding agents bind to different epitopes of the same analyte with differing affinities. The difference in affinities may be 2-fold, 4-fold, 10-fold or more.

In some embodiments, the sample is a biological sample, such as but not limited to a whole blood sample or a serum sample.

In some embodiments, the analyte is a biomarker such as for example a cancer antigen. An example of such a cancer antigen is prostate specific antigen (PSA).

In some embodiments, the nanoswitches comprise a first modification at a first end and a second modification at a second end, wherein the first and second modifications are different from each other.

In some embodiments, the nanoswitches comprise a first member of a first binding pair on a first end and a second member of a second binding pair at a second end.

In some embodiments, the nanoswitches are tethered to a surface using a first member of a binding pair that is present on a first end of the nanoswitch and a second member of a binding pair that is present on the surface. For example, the binding pair may be an antigen-antibody pair, where the first member is an antigen and the second member is an antibody or an antigen-binding antibody fragment. An example of such a binding pair an digoxigenin and anti-digoxigenin antibody binding pair. In some embodiments, the first member at the first end is either a digoxigenin or anti-digoxigenin antibody and the second member at the second end is either biotin or streptavidin.

In some embodiments, the plurality of nanoswitches comprises a first subset of nanoswitches that bind to a first analyte and a second subset of nanoswitches that bind to a second analyte, wherein when bound to their respective analytes nanoswitches in the first subset have a length that is discernably different from length of nanoswitches in the second subset. The difference in length of the nanoswitches may be in the range of about 0.25-2.0 microns, including 0.5-1.5 microns, including 0.5-1.0 microns. In some embodiments, the difference in length is about 2 nm to about 10 nm, or about 2 nm to about 50 nm, or about 2 nm to about 200 nm. In some embodiments, the difference is about 10 nm to about 100 nm, or about 50 nm to about 100 nm, or about 100 nm to about 200 nm, or about 150 nm to about 300 nm, or about 200 nm to about 400 nm or to about 600 nm or to about 800 nm or to about 1 micron. The methods and devices used to detect such length differences may vary depending on their ability to resolve bead-tracking. For example, in some instances the distance may be measured using a centrifuge force microscope (e.g., differences on the order of about 2 nm or more) while in other instances the distance may be measured using flow and simple microscopy (as used in the Examples) (e.g., differences on the order of 200 nm or more).

Thus, in some embodiments, the method is a method of detecting a first and a second analyte using the first and second subsets of nanoswitches. It is to be understood that a plurality of analytes may be detected using a plurality of nanoswitches of distinct length in a closed conformation.

In some embodiments, trajectories of single surface-tethered nanoswitches under forward and reverse force are observed before or after length and/or rupture events are measured or detected. Nanoswitches having symmetrical forward and reverse trajectories may be identified. Symmetrical trajectories means that the displacement in one axis (e.g., an x-axis) under forward force, $X_1$, is roughly the same as the displacement in the same axis under reverse force, $X_2$. In some instances, symmetrical trajectories may have a symmetry, $s=X_1/X_2$ between 1+/−standard error of the mean (SEM). In other instances, symmetrical trajectories have a symmetry of s' where $s'=X_1/X_2$ and is between 1+/−Epsilon, where Epsilon is chosen to minimize false positive and false negative signals, and is a function of the measurement error. For example, Epsilon could be chosen as the relative SEM under no force. Alternatively, a nanoswitch has symmetrical trajectories if $asym=(X_1-X_2)/((X_1+X_2)/2)$ is less than Epsilon, where Epsilon is chosen to minimize false positive and false negative signals, and is a function of the measurement error.

In some embodiments, the length of a nanoswitch is measured and/or a rupture event of a nanoswitch is detected using a light microscope, such as but not limited to a fluorescence microscope. Such microscope may be equipped with a camera in order to monitor the movement of the nanoswitch and/or the particle.

In some embodiments, step (a) is performed in solution.

In some embodiments, the nanoswitches are conjugated at one end to a particle prior to contact with the sample.

This disclosure provides, in another aspect, a method for detecting an analyte in a sample comprising (a) contacting a sample with a plurality of nanoswitches each end-conjugated to a particle for a time and under conditions sufficient for binding of an analyte to a nanoswitch thereby forming a mixture of closed and open nanoswitches, (b) tethering closed and open nanoswitches to a surface, (c) identifying surface-tethered closed nanoswitches having symmetrical trajectories under forward and reverse forces, and (d) measuring length of single surface-tethered closed nanoswitches and/or detecting rupture event of single surface-tethered closed nanoswitch, under force, wherein the nanoswitch is a nucleic acid conjugated to a first and a second analyte-binding agent which when bound to the analyte adopts a looped conformation and a shorter length as compared to the length of the nanoswitch when it is not bound to the analyte.

It is to be understood that the nanoswitches may be contacted with sample first, then conjugated to beads, and then conjugated to a surface. Other variations are also contemplated. For example, the nanoswitches may be contacted with the surface first, then the beads, and then the sample although this may result in a lower LOD than other orders of contact. When the nanoswitches are first contacted with the sample, then conjugated to the beads, and then finally attached to the surface, higher LOD were observed.

This disclosure provides, in another aspect, a method for detecting an analyte in a sample comprising (a) contacting a sample with a plurality of nanoswitches for a time and under conditions sufficient for binding of an analyte, if present in the sample, to its respective nanoswitch to create a closed nanoswitch, (b) tethering the closed nanoswitch to a surface, and (c) measuring length or a change in length of a single surface-tethered closed, under force, wherein the nanoswitch is a nucleic acid conjugated to a first and a second analyte-binding agent which when bound to the analyte adopts a looped conformation and a shorter length as compared to the length of the nanoswitch when it is not bound to the analyte.

In some embodiments, the method further comprises, between steps (a) and (b), enriching and isolating closed nanoswitches.

In some embodiments, length or change is length is measured under constant force. In some embodiments, length or change is length is measured under dynamic force.

This disclosure provides, in another aspect, a method for detecting an analyte in a sample comprising (a) providing a surface-tethered complex, wherein the complex comprises an analyte bound to a first and a second analyte binding agent, wherein the first analyte-binding agent is coupled to a bead and the second analyte-binding agent is coupled to a surface, (b) applying a force to the complex, and optionally identifying surface-tethered complexes having symmetrical trajectories under forward and reverse forces, (c) measuring, for individual surface-tethered complexes, length of the complex under force, and/or the force required to rupture the complex (e.g., to rupture the bead from the second analyte-binding agent) under dynamic force, and/or lifetime of the complex under constant force.

In some embodiments, the first analyte-binding agent is coupled to the bead with a nucleic acid. In some embodiments, the second analyte-binding agent is coupled to the surface with a nucleic acid.

This disclosure provides, in another aspect, a method for detecting an analyte in a sample comprising (a) contacting a sample with a first analyte-binding agent coupled to a bead, optionally coupled through a nucleic acid, under conditions sufficient to allow binding of the first analyte-binding agent to its respective analyte, if present in the sample, to form an intermediate complex, (b) contacting the intermediate complex with a second analyte-binding agent coupled to a surface, optionally coupled through a nucleic acid, under conditions sufficient to allow binding of the second analyte-binding agent to the analyte, to form a surface-tethered complex, (c) applying force to the surface-tethered complex, and (d) measuring length of the surface-tethered complex, and/or force at which the complex ruptures, and/or time it takes the complex to rupture.

In some embodiments, the force is constant force and step (d) comprises measuring the length of the surface-tethered complex and/or time it takes the complex to rupture. In some embodiments, the force is increasing force and step (d) comprises measuring the force at which the complex ruptures. In some embodiments, a constant force is applied and the length of the complex is measured and then an increasing force is applied and the force at which the complex ruptures is measured.

This disclosure provides, in another aspect, a method for detecting an analyte in a sample comprising (a) contacting a sample with a plurality of nanoswitches, each nanoswitch conjugated at a first end to a lipid and at a second end to a particle, for a time and under conditions sufficient for binding of an analyte to a nanoswitch, thereby forming a mixture of closed and open nanoswitches, (b) aligning and extending the closed and open nanoswitches in a fluid lipid bilayer using force, and (c) identifying, and optionally measuring, closed nanoswitches based on length, wherein the nanoswitch is a nucleic acid conjugated to a first and a second analyte-binding agent which when bound to the analyte adopts a looped conformation and has a shorter length as compared to the length of the nanoswitch when it is not bound to the analyte.

In some embodiments, the nanoswitches of (a) are in solution, and after the time sufficient for binding to an analyte are inserted into the lipid bilayer.

In some embodiments, the nanoswitches are labeled with a detectable stain or dye.

In some embodiments, the particle is a fluorescent particle. In some embodiments, the particle is a quantum dot.

In some embodiments, the analyte-binding agents are antibodies or antigen-binding antibody fragments.

In some embodiments, the force is hydrodynamic force. In some embodiments, the force is centrifugal force or magnetic force.

In some embodiments, the ratio of closed to open nanoswitches ranges from $1:10^{-1}$ to $1:10^8$. As will be understood in view of the present disclosure, if the analyte is at a very high concentration, there may be more closed nanoswitches than open nanoswitches. In these instances, the ratio of closed to open nanoswitches may range from $1:10^{-2}$ to 1 or from $1:10^{-1}$ to 1. If, on the other hand, the analyte is very rare, then there will be more open nanoswitches than closed nanoswitches. In these instances, the ratio of closed to open nanoswitches may range from $1:10^2$ to $1:10^6$ or from $1:10^2$ to $1:10^8$.

In some embodiments, the lipid bilayer is disposed on a solid support. In some embodiments, the solid support comprises $SiO_2$.

In some embodiments, the solid support comprises a barrier. The lipid to which the nanoswitch is conjugated may not flow past such barrier, in some instances. In some embodiments, the barrier is a mechanical barrier. In some embodiments, the mechanical barrier is a scratch on the solid support. In some embodiments, the barrier is a chemical barrier. In some embodiments, the chemical barrier comprises a metal, a metal oxide, or a combination thereof. In some embodiments, the metal comprises chromium, aluminum, gold, or titanium. In some embodiments, the metal oxide comprises chromium oxide, aluminum oxide, or titanium oxide. In some embodiments, the barrier is a protein barrier.

In some embodiments, the lipid bilayer comprises zwitterionic lipids.

In some embodiments, the sample is a biological sample. In some embodiments, the sample is a whole blood sample or a serum sample.

In some embodiments, the analyte is a cancer antigen. In some embodiments, the analyte is prostate specific antigen (PSA).

In some embodiments, the analyte is present in the sample at a concentration ranging from about 10 attomolar to about 10 femtomolar. In some embodiments, the analyte is present in the sample at a concentration ranging from about 10 femtomolar to about 100 picomolar.

In some embodiments, the nanoswitches are present at a concentration that is $10^3$ to $10^8$ greater than analyte concentration. In some embodiments, the nanoswitches are present in a concentration ranging from about 150 picomolar to about 1.5 nanomolar.

This disclosure provides, in another aspect, a product comprising:

(a) a solid support,
(b) a fluid lipid bilayer disposed on the solid support, and
(c) a plurality of nanoswitches.

In some embodiments, the solid support comprises a barrier.

In some embodiments, the solid support and fluid lipid bilayer are present in a cartridge.

In some embodiments, the plurality of nanoswitches is provided a housing separate from the solid support and fluid lipid bilayer.

In some embodiments, the nanoswitches are lipid-conjugated. In some embodiments, the nanoswitches are lipid-conjugated at a first end. In some embodiments, the nanoswitches are conjugated to a particle at a second end. In some embodiments, the particle is a fluorescent particle. In some embodiments, the fluorescent particle is a quantum dot. nanoswitches are inserted into the fluid lipid bilayer.

In some embodiments, a subset of nanoswitches is bound to an analyte.

In some embodiments, the product further comprises a sample.

In some embodiments, the fluid lipid bilayer is disposed on the solid support.

In some embodiments, the product is situated in a flow cell. In some embodiments, the product is situated in a microfluidic flow cell.

In some embodiments, the nanoswitches are labeled with a detectable stain or dye.

In some embodiments, the solid support comprises $SiO_2$

In some embodiments, the fluid lipid bilayer comprises zwitterionic lipids.

In some embodiments, the plurality of nanoswitches comprises a first subset of nanoswitches that bind a first analyte and a second subset of nanoswitches that bind a second analyte that is different from the first analyte, and wherein when bound to their respective analytes nanoswitches in the first subset have a discernably different length from the nanoswitches in the second subset.

These and other aspects and embodiments of this disclosure will be described in greater detail herein.

In some embodiments, the nanoswitch and/or tethers are constructed from DNA, though they can also be formed from other polymers, such as PEG.

BRIEF DESCRIPTION OF DRAWINGS

The accompanying drawings are not intended to be drawn to scale. Certain of the accompanying drawings may be in color and these may be accessed through the file wrapper at the United States Patent and Trademark Office.

(FIG. 1A) Assembly of the programmable nucleic acid nanoswitch. The analyte-binding agents (which may also be referred to as analyte-binding probes), Y, are coupled to oligonucleotides that hybridize to specific locations on a linearized single stranded nucleic acid scaffold. Nanoswitches switch from an open (or linear) conformation to a closed (or looped) conformation once an analyte is captured. (FIG. 1B) Gel-electrophoresis separation of the looped nanoswitches from the linear ones. The intensity of the top, more slowly migrating, band containing the looped nanoswitches, corresponds to the amount of analyte in the sample.

(FIG. 1C) Schematic of the experimental setup for a Flow Cell experiment with nanoswitches (NS) tethered between a micron bead and a flat surface. (FIG. 1D) Field of view through an optical microscope with 20× magnification. The inset shows an exemplary bead trajectory under reverse flow at three distinct time points. (FIG. 1E) Typical tether extension over time of a reverse flow experiment, the distinct time points of FIG. 1D are marked.

As described herein, the nanoswitches may be detected by the position of their end-conjugated bead under flow. By flowing the nanoswitches and thus the beads to the left and then to the right (or vice versa), closed nanoswitches can be identified by their symmetric trajectories (i.e., distance when stretched to the left equals distance when stretched to the right) and/or by their length (which can be measured by looking at the displacement of the bead during flow stretching).

It is to be understood that depending on the reaction conditions and kinetics, not all nanoswitches may be cleaved. As a result, there may be still be some fraction of linear nanoswitches bound to the surface. Nevertheless, it is expected that the procedure will increase the ratio of closed to open nanoswitches even if not all linear nanoswitches are cleaved.

FIGS. 1G-1J illustrate further embodiments for performing force measurements on single molecules. FIG. 1G illustrates first and second analyte-binding agents and target analyte. FIG. 1G, right most panel, illustrates a bead tethered to an analyte-binding agent through a hybridization event between two nucleic acids, one coupled to the bead and one coupled to the analyte-binding agent. Of notable interest is the internal location of the analyte-binding agent on the partially duplexed nucleic acid tether, rather than at the free end of the duplexed region. Such internal positioning may result in "unzippering" of the duplexed region upon the application of force to the bead. It has been found that the internal positioning, as compared to the free-end positioning, allows the strength of the duplex (and the force required to disrupt the duplex) to be fine-tuned. This enables customized complexes with signature characteristics, such as rupture force, for each specific analyte.

FIG. 1H illustrates an analyte-binding agent tethered to a surface. The Figure illustrates that the length of the tether can be modulated, thereby creating customized complexes with signature characteristics, such as complex length when force is applied, for each specific analyte. An alternative embodiment contemplates modifying the length of the tether that couples the bead to the first analyte-binding agent.

FIG. 1I illustrates a surface-tethered complex comprising an analyte bound to two different analyte-binding agents, one of which is coupled to the surface and the other coupled to a bead. Tethers used to couple beads and surface to their respective analyte-binding agents may comprise partially double-stranded nucleic acids, an example of which is shown in the Figure.

Figure 1B:
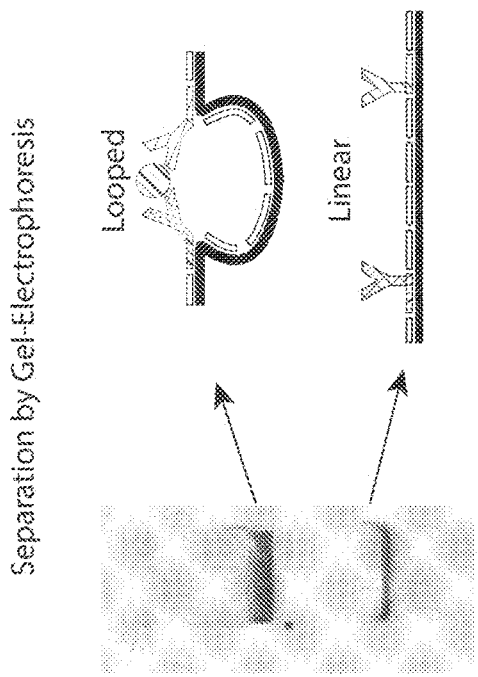
FIGS. 1A to 1B.
Figure 1B:
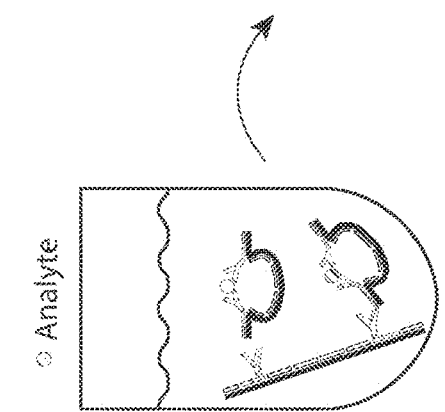
Figure 1A:
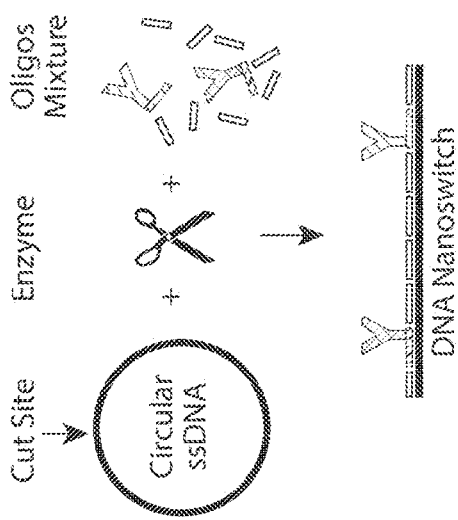
Figure 1C:
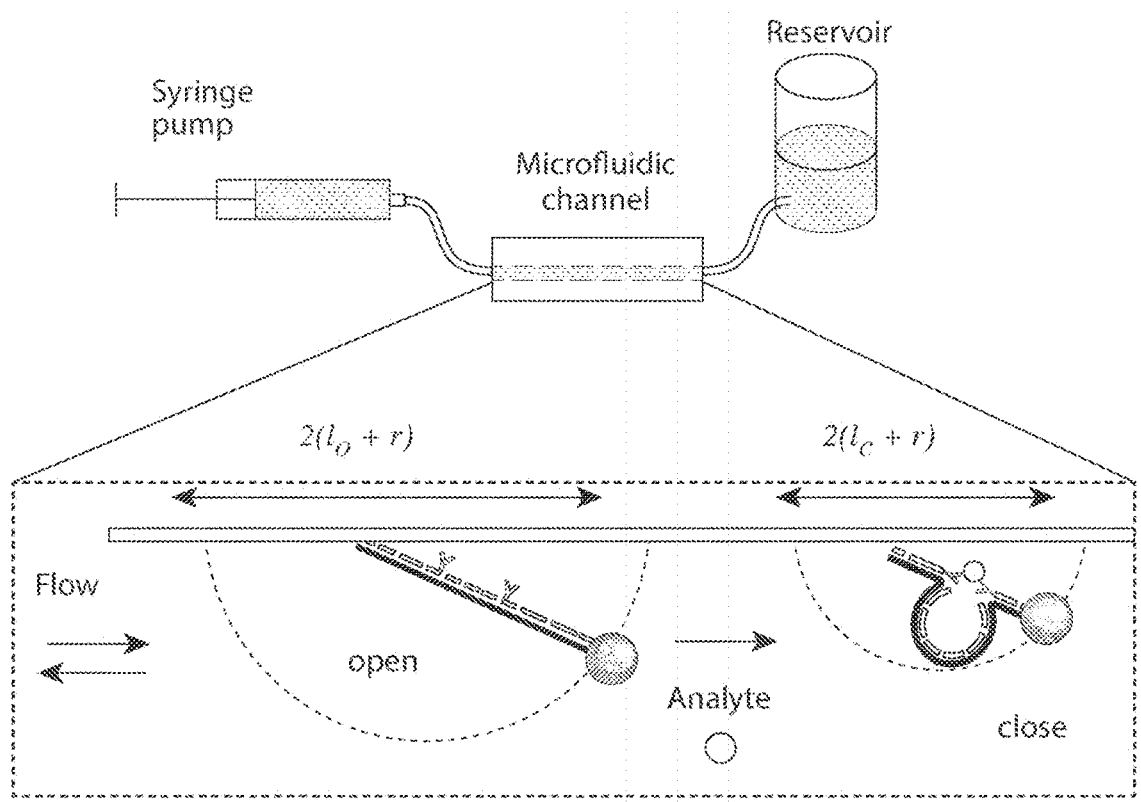
FIGS. 1C to 1E. Overview of the force-controlled immunoassay.
Figure 1D:
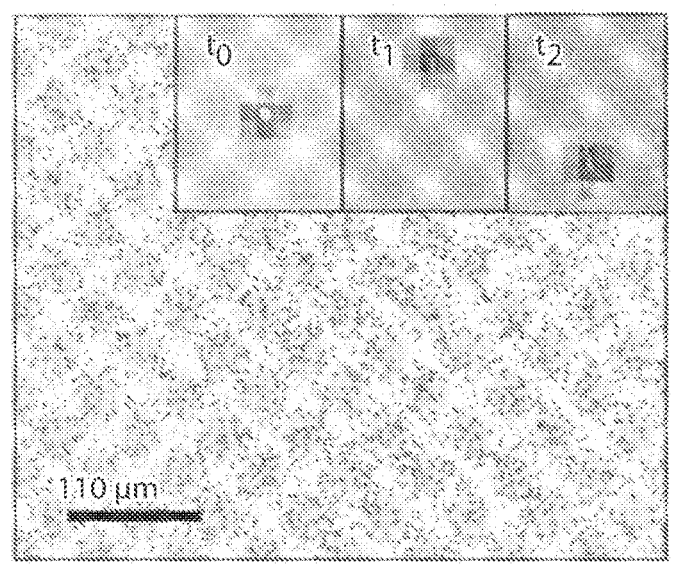
Figure 1E:
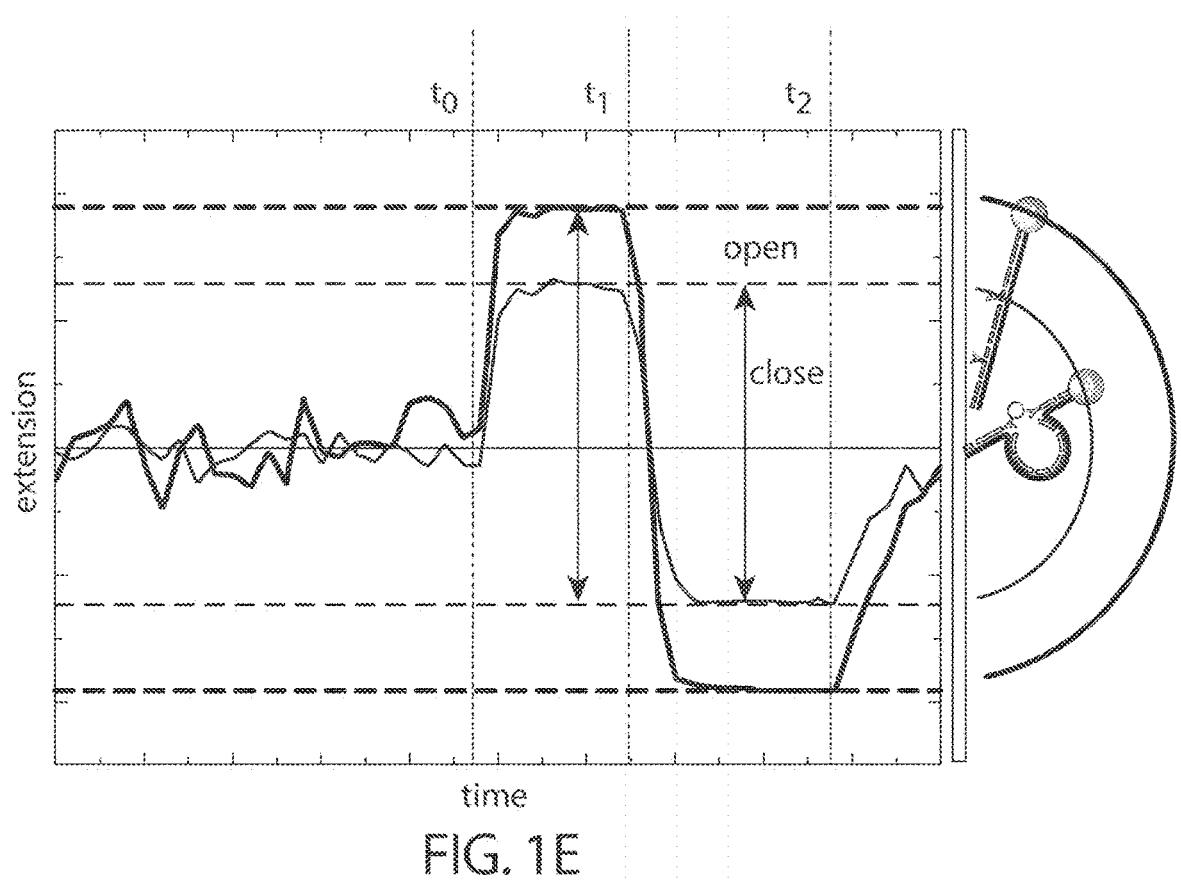
Figure 1F:
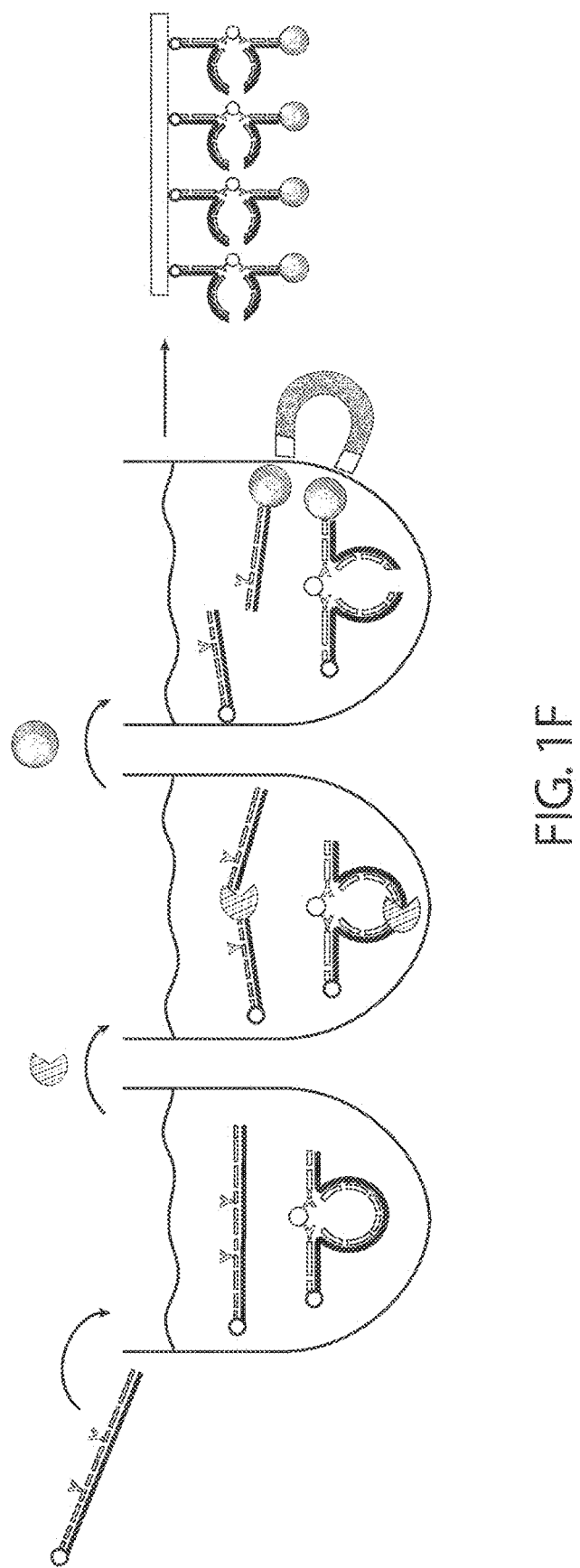
FIG. 1F. Increasing detection sensitivity using cutting enzymes. In the left most panel, nanoswitches are mixed with sample, and binding events induce conformational change in the nanoswitch. The nanoswitches are functionalized on a first end for ultimate attachment to a surface, as shown in the right most panel. In the next panel, a cutting enzyme (alternatively referred to herein as a cleavage or restriction enzyme) is added and allowed to cut the nanoswitch. The nanoswitch is designed to have cleavage sites within its looped region. In some embodiments, the nanoswitch is designed to have two such cleavage sites in its looped region. The enzyme will cut nanoswitches in the looped and linear conformations, as illustrated. In the next panel, a bead, such as a magnetic bead, is added to the mixture and allowed to bind to the second end of the nanoswitches (and nanoswitch fragments which result from the cleavage of the enzyme on the linear nanoswitch). If the beads are magnetic, then a magnet is then used to isolate the nanoswitches and nanoswitch fragments that are labeled with the magnetic particle, followed by a wash in order to remove the nanoswitches and nanoswitch fragments that are not magnetically labeled. If the beads are non-magnetic, then the mixture may be spun down at a force that brings down the bead but not the unconjugated fragments and the supernatant may be removed, one or more times, in order to remove the fragments that are not bead-conjugated. After washing, the isolated nanoswitches (e.g., either magnetically or by centrifugation) are attached to a surface using the functionality at their first ends, as shown in the right most panel. The nanoswitch fragments that lack their first ends will not bind to the surface. In this way, the closed nanoswitches can be selectively bound to the surface such as but not limited to a flow cell surface, thereby increasing the sensitivity of detecting such closed nanoswitches.
Figure 1J:
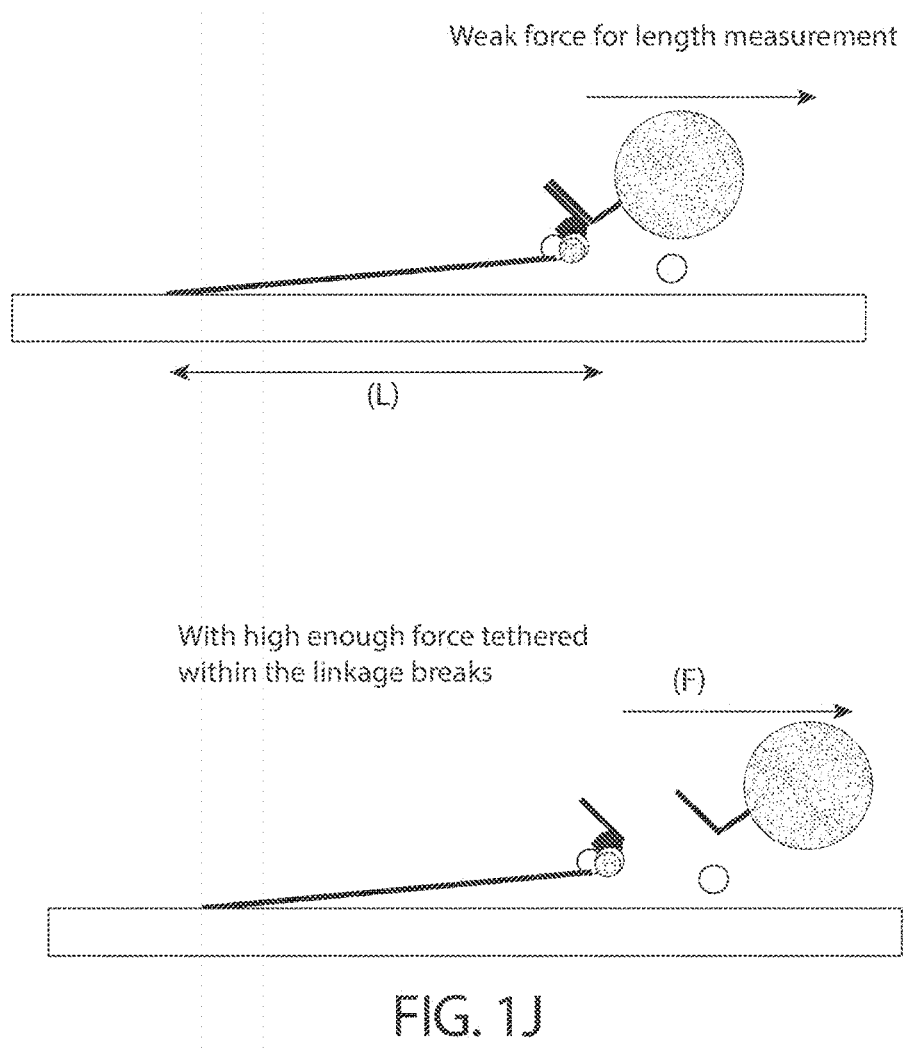

FIG. 1J illustrates measurement of (a, top panel) complex length under a force that is insufficient to rupture the complex and (b, bottom panel) rupture force required to remove the bead from the complex. Either or both measurements may be made on individual complexes.

Figure 2A:
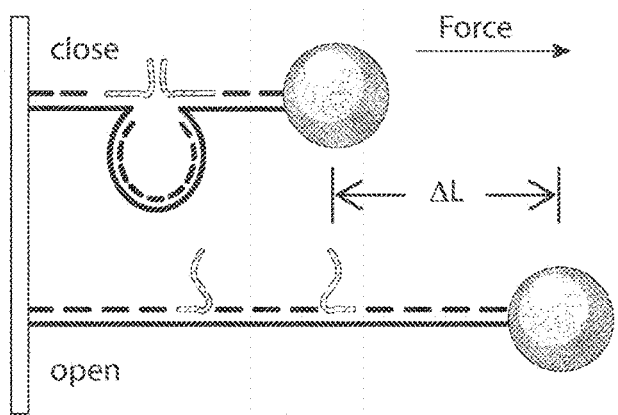
Figure 2B:
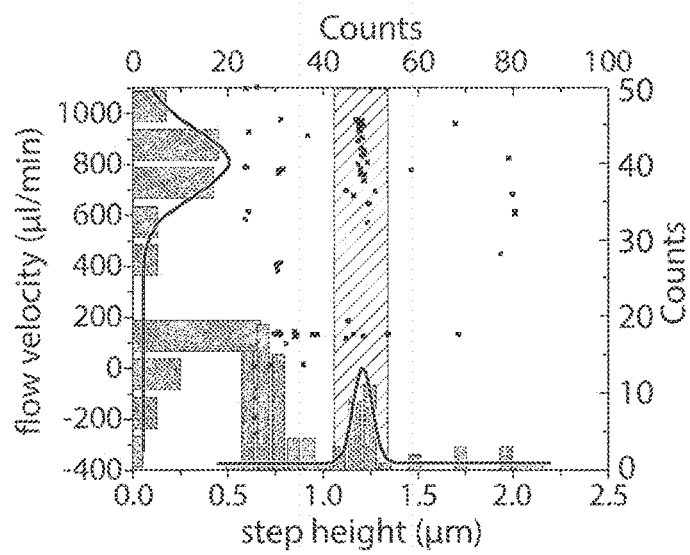
Figure 2C:
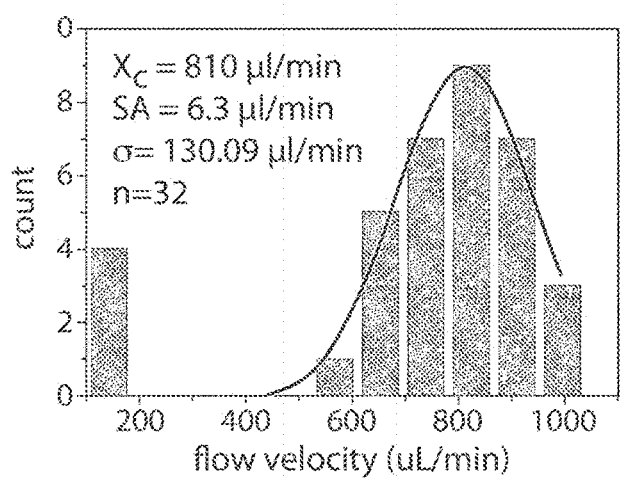

FIGS. 2A to 2C. Force calibration of FCI. (FIG. 2A) Schematic of the unzipping construct. (FIG. 2B) Scatter plot of flow velocity versus step height ($\Delta L$) of rupture events recorded in a ramp-experiment with 138 tethers. Histograms project flow velocity and step height to the x- and y-axes, respectively. The most probable flow velocity at rupture and the corresponding step height are fitted with a GAUSSIAN function. (FIG. 2C) Flow velocity at rupture filtered by step height in FIG. 2B.

Figure 3A:
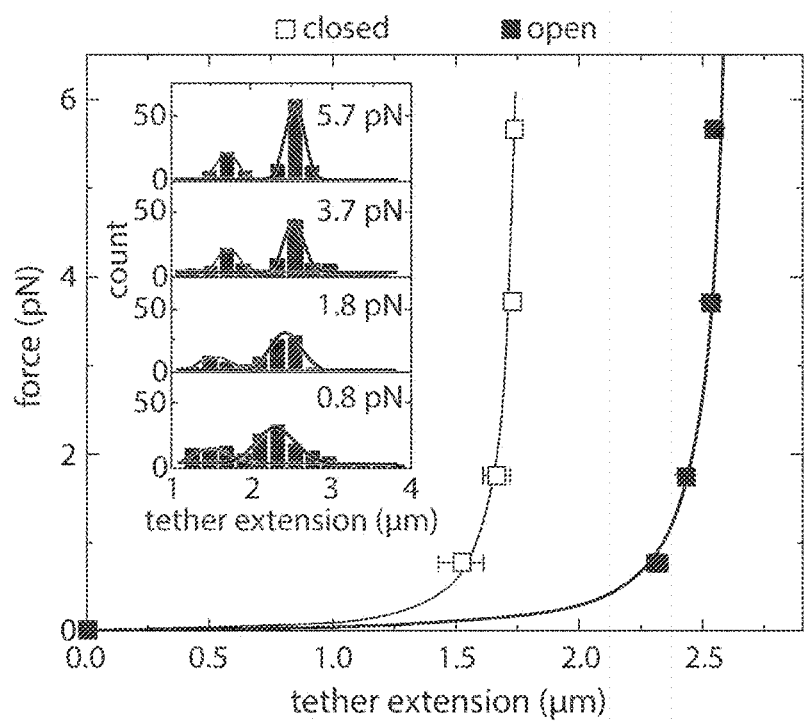
Figure 3B:
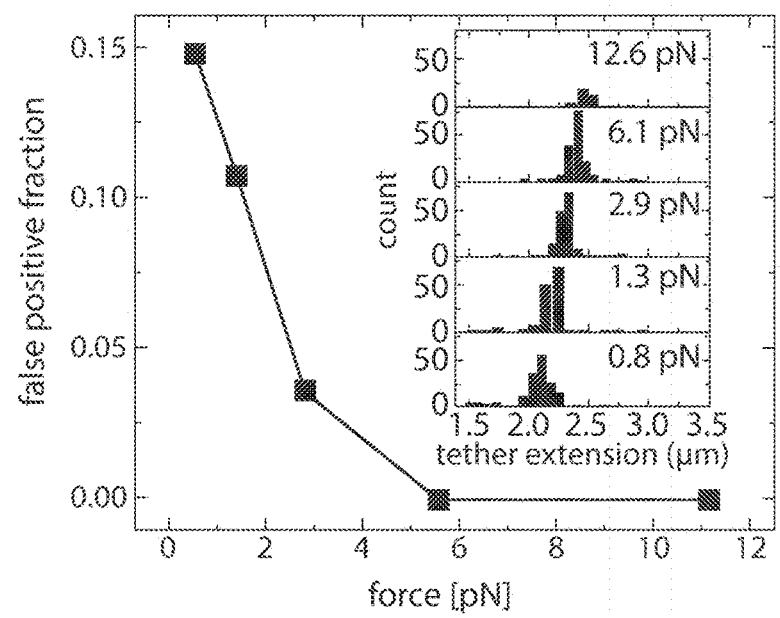
Figure 3C:
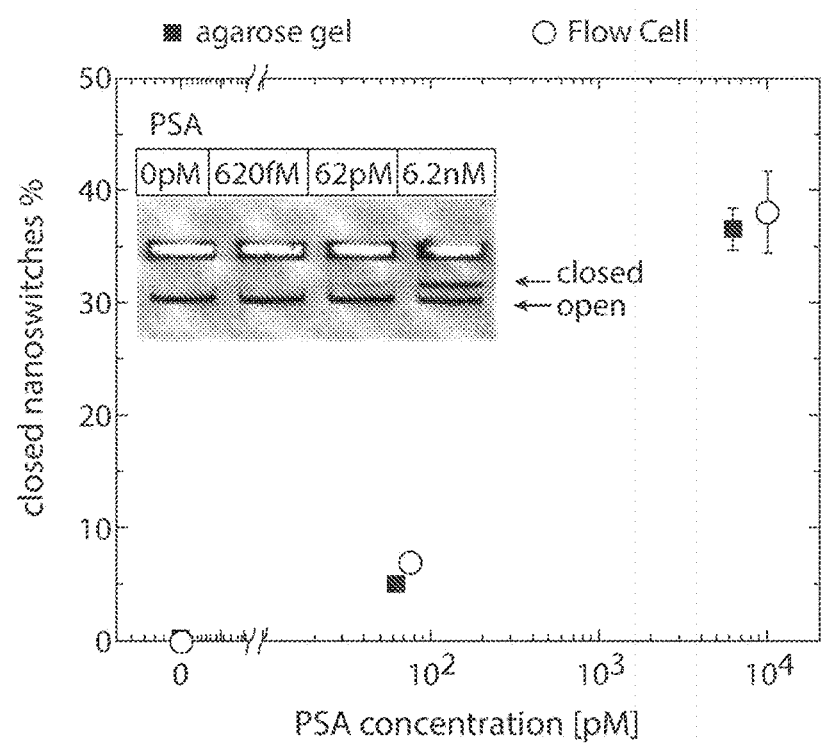

FIGS. 3A to 3C. Characterization of Anti-PSA nanoswitches. (FIG. 3A) Force-extension curves obtained in a flow cell for open and closed tethers in the presence of 100 pM PSA. The solid lines represent Worm Like Chain (WLC) for the corresponding contour and persistence length. The error bars represent the standard deviation of the Gaussian fit to the histograms in the inset. (FIG. 3B) False positive rate of open NS in the absence of PSA as a function of pulling force. The inset shows histograms recorded at different pulling force. (FIG. 3C) Comparison of PSA detection using gel-electrophoresis on a 0.9% agarose gel stained with Sybr gold and the Flow Cell assay. The inset shows the result of a typical agarose gel detection experiment with different biomarker concentrations.

Figure 4A:
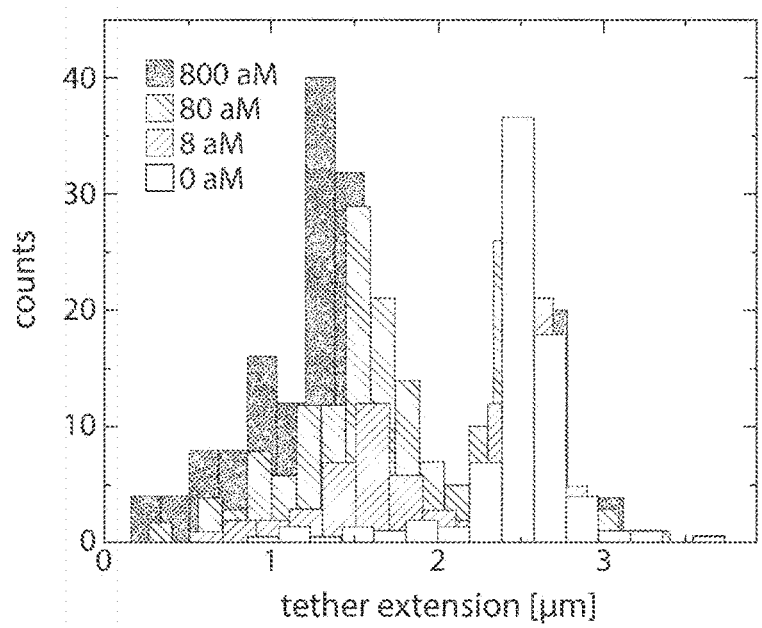
Figure 4B:
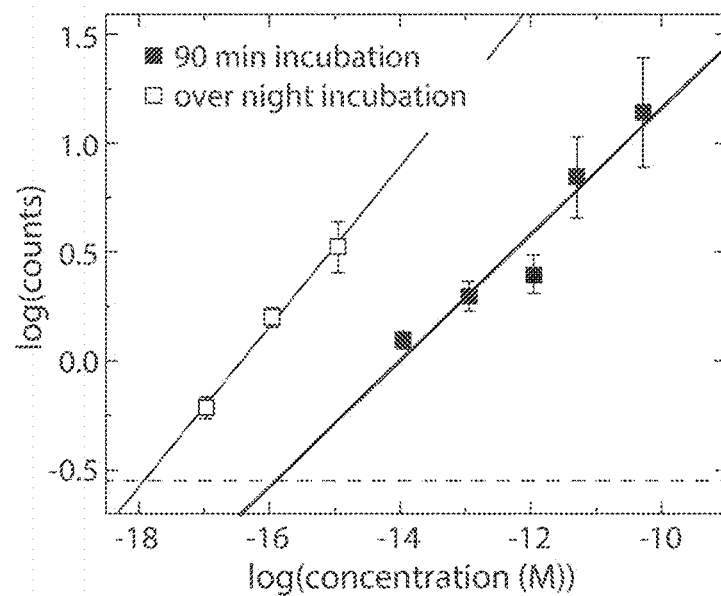
Figure 4C:
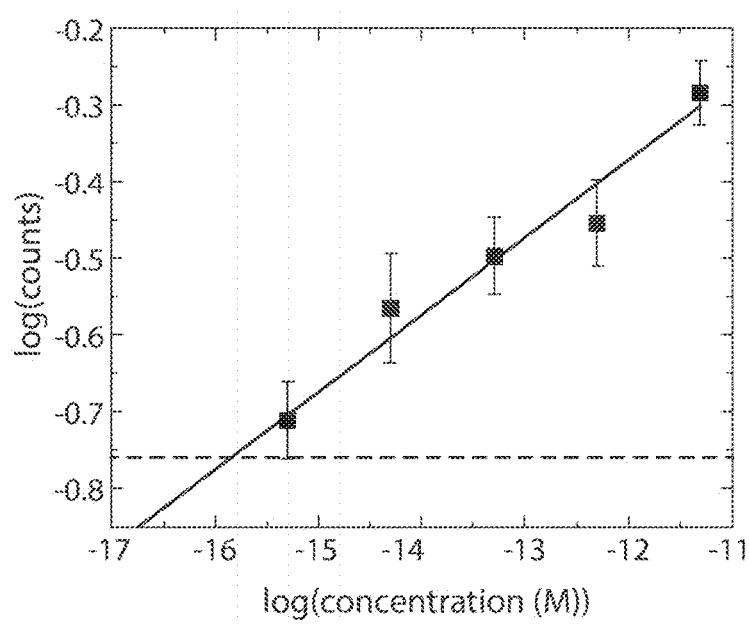

FIGS. 4A to 4C. Ultra-sensitive biomarker detection. (FIG. 4A) Typical histograms of tether length for different biomarker concentrations. (FIG. 4B) Count of closed nanoswitches normalized by the number of open nanoswitches as a function of biomarker concentration in PBS buffer for different nanoswitch concentrations and incubation times. The cross section between the logarithmic fit (straight line) and background signal plus three standard deviations (dotted line) reflects LOD of 1.2 aM PSA for overnight incubation and 91 aM for 90 min incubation time. (FIG. 4C) Dose-response curve of PSA spiked into 20% bovine serum with LOD of 138 aM for a 90 min incubation time. Error bars reflect standard deviation of three independent experiments.

Figure 5A:
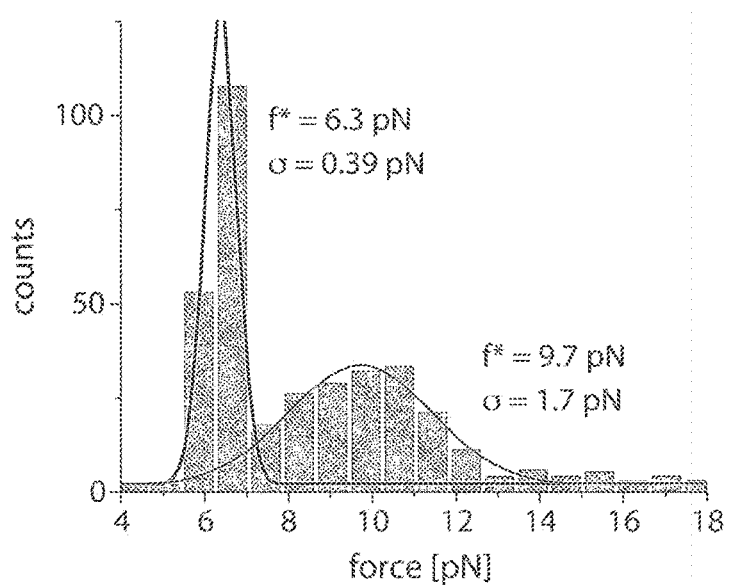
Figure 5B:
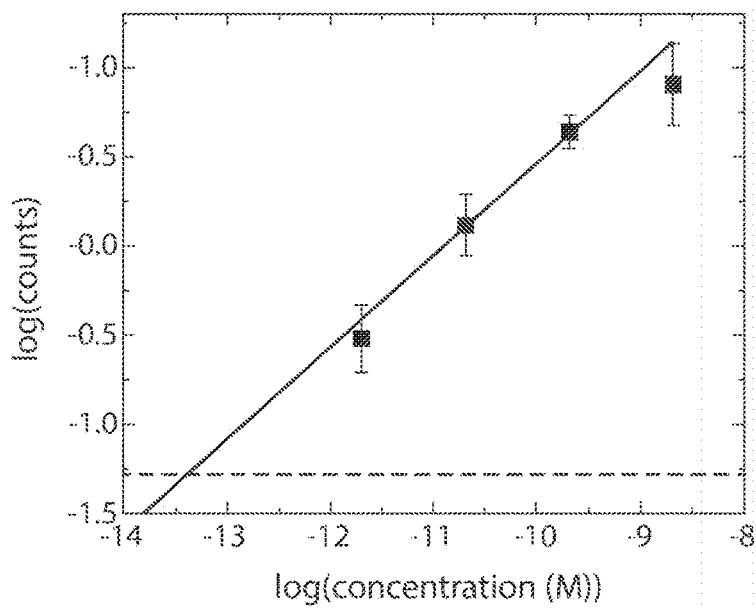

FIGS. 5A to 5B. Biomarker detection in whole blood. (FIG. 5A) Histogram of rupture forces of anti-PSA functionalized NS after isolation from whole blood spiked with 2 nM PSA. Peaks are fitted with Gaussian function and most probable rupture force (f*) and standard deviation ($\sigma$) are given as numbers. (FIG. 5B) Dose-response curve of PSA spiked into whole blood serum with 1.5 nM nanoswitch concentration and 90 min incubation time reveals LOD of 13 fM for whole blood. Error bars reflect standard deviation of three independent experiments.

Figure 6A:
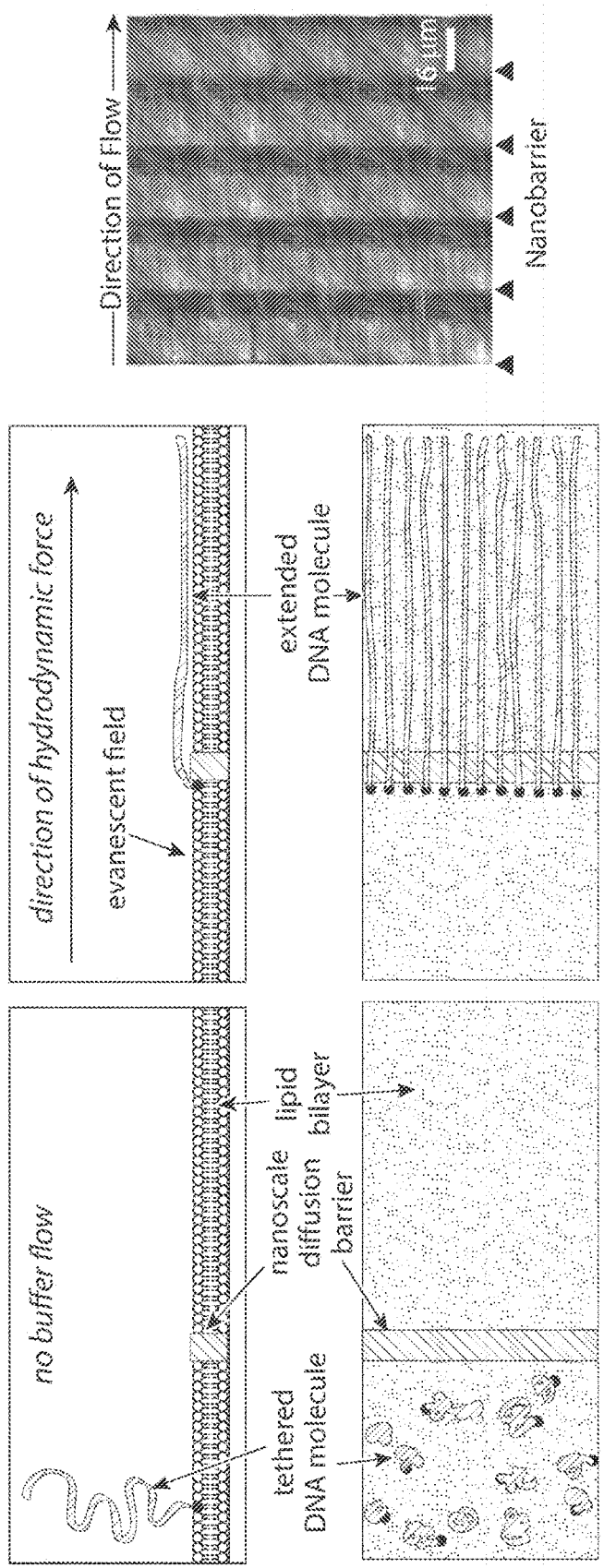
Figure 6B:
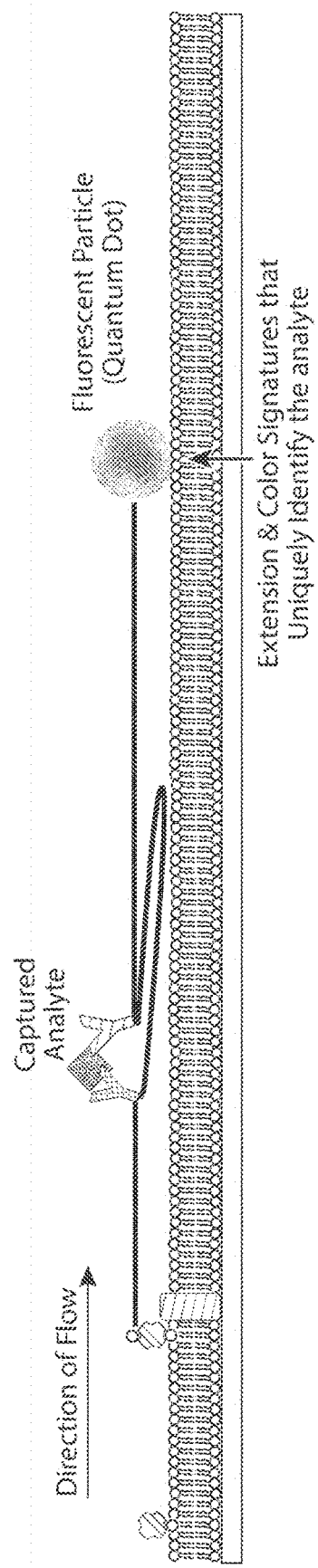

FIGS. 6A to 6B. (FIG. 6A) Diagram of DNA curtains. The surface consists of the lipid bilayer along with structural metallic nanobarriers. When the hydrodynamic flow is applied, the DNA tethers are dragged toward the barrier and fully stretched out. Figure on the right shows thousands of extended and aligned λ-DNA. Figures adapted from [19, 20]. (FIG. 6B) Illustration of functionalized looped DNA Nanoswitch incorporated into the DNA curtains. Imaging the fluorescence at a specific location can identify the particular analyte captured in a multiplex assay.

Figure 7:
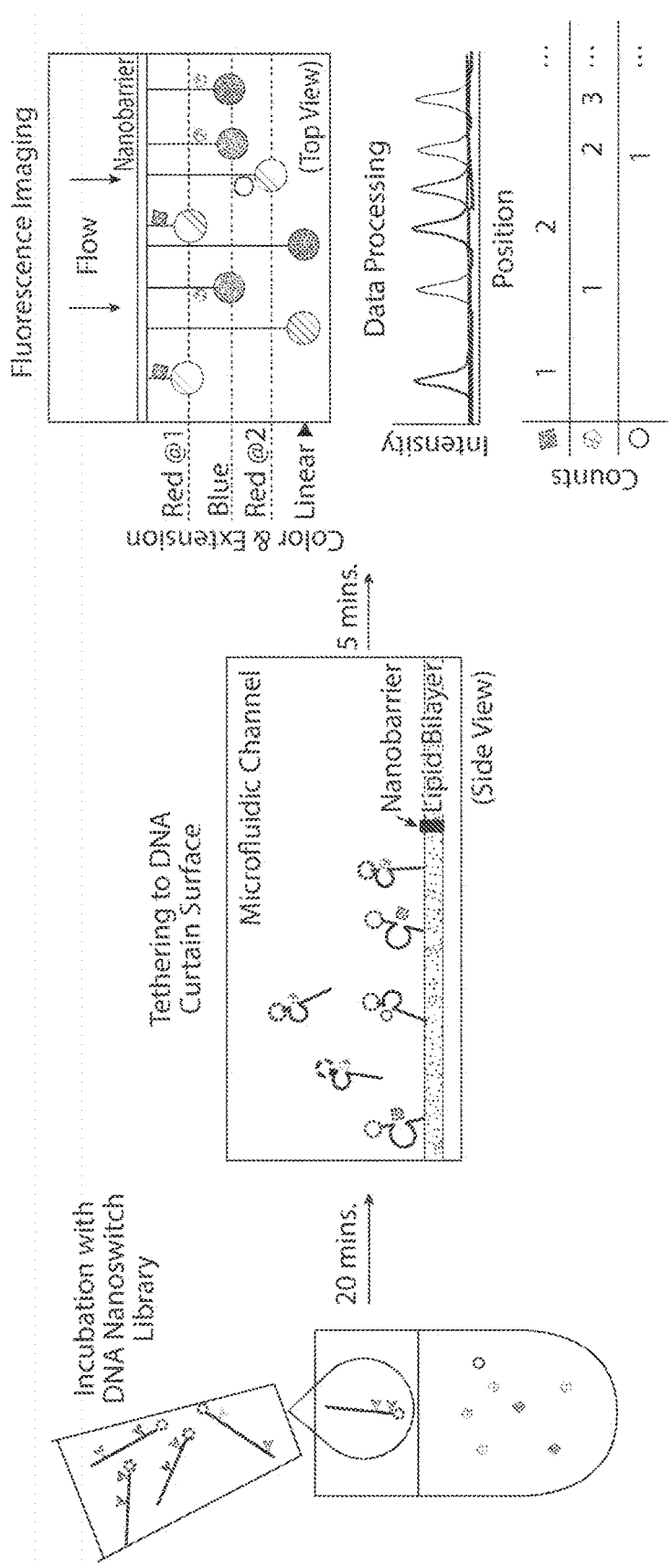

FIG. 7. Workflow of the multiplexed DNA nanoswitch curtains detection assay. With the nanoswitch reagents prepared for the end-user, it starts with the incubation step of the nanoswitch library in the sample. Afterward, the sample containing the nanoswitches is loaded in the DNA curtains microfluidic channel, and the nanoswitches will tether onto the lipid bilayer. The imaging is performed with a fluid flow so that the nanoswitches will accumulate and extend along the nanobarriers. Multiples images are captured across entire channel with different fluorescence colors. Image analysis will primarily consist of scanning along the barrier direction to detect the signal that corresponds to the analytes.

DETAILED DESCRIPTION OF CERTAIN EMBODIMENTS

This disclosure relates to the detection and optionally measurement of analytes, including rare analytes such as rare biomarkers, using nanoswitches. Provided herein are methods of detection using nanoswitches, and associated products. These methods may be used to detect and optionally measure analytes from complex biological samples such as but not limited to whole blood and serum. The ability to measure biomarkers provides a much more comprehensive view of a biological system. This is particularly important for clinical applications since changes in protein expression can indicate the presence of disease states, such as cancer [15]. In the case of infections, the body's response can be tracked through the measurement of specific antibodies and cytokines produced. One recent technique to perform single-molecule detection, digital-ELISA, has demonstrated sub-fM sensitivity for many clinically relevant protein biomarkers [17]. The approaches provided herein are capable of achieving even greater sensitivity.

There are two general approaches described herein. The first approach, force-controlled immunoassay (FCI)/lateral force microscope (LFM) involves tethering a nanoswitch to a surface, optionally confirming single-nanoswitch events using a forward and reverse flow analysis, and measuring the length of the nanoswitch under force and/or the force of the rupture event in the nanoswitch. The lengths of the nanoswitch when in the open (linear) and closed (looped) conformations is known ahead of time and thus can be used as a surrogate for the presence of an analyte. Similarly, the analyte-binding agents (or probes) are known ahead of time. In some instances, their binding strength for the analyte is also known ahead of time. As a result, the force required to rupture the binding between the analyte and the weaker of the analyte-binding agents is known ahead of time and can also be used as a surrogate for the presence of the desired analyte or as a confirmation that the nanoswitch has bound the desired analyte. In other instances, the binding strength of the analyte-binding agents for the analyte may not be known ahead of time. However, by carrying out a control experiment in the absence of the analyte, one can identify the strength of background interactions. Then in the presence of the test sample, any interactions that are stronger (or different) than the strength of background interactions may be putatively treated as interactions with the desired analyte.

The second approach, nanoswitch curtains, involves inserting a nanoswitch into a fluid surface, such as a lipid bilayer, and then aligning and simultaneously observing a plurality (e.g., thousands) of nanoswitches, in order to identify nanoswitches in closed (or bound) conformations. The closed, looped conformations are identified as they are shorter than the open, linear conformations.

These approaches are described in greater detail below.
Nanoswitches Generally

Nanoswitches are programmable constructs initially designed to facilitate reliable single-molecule force spectroscopy measurements [7], and then were subsequently used to make kinetic measurements of multi-component interactions [12] and to characterize mechanical heterogeneity of molecular binding [6, 18] The nanoswitch can transition between at least two distinct configurations depending upon the binding of one or more target analytes.

As used herein, a nanoswitch is a nucleic acid attached, along its length, to least two analyte-binding agents (or probes). The analyte-binding agents typically bind to the same analyte, but may bind to the same or a different epitope on such analyte. In some embodiments described herein, it may be preferred that the analyte-binding agents bind to different epitopes of the analyte, and even more preferably that the analyte binding strength of one agent is greater than the analyte binding strength of the other. This allows for the rupture of the bond between the analyte and one agent but not the simultaneous rupture of the bonds between the analyte and both agents.

The analyte-binding agents may be coupled to an end of an oligonucleotide such as the 5' or the 3' end, or it may be coupled at an internal location of the oligonucleotide. In some instances, a first analyte-binding agent may be coupled to the 3' end of a first oligonucleotide and the second analyte-binding agent may be coupled to the 5' end of a second oligonucleotide. Such orientation may result in the analyte-binding agents being closer to each other, as illustrated in FIG. 1A, or such orientation may result in the analyte-binding agents being farther away from each other. In some instances, a first analyte-binding agent may be coupled to the 3' end of a first oligonucleotide and the second analyte-binding agent may be coupled to the 3' end of a second oligonucleotide. In some instances, a first analyte-binding agent may be coupled to the 5' end of a first oligonucleotide and the second analyte-binding agent may be couple to the 5' end of a second oligonucleotide.

The nanoswitch may be partially or fully double-stranded. It may be a double-stranded nucleic acid having a plurality of backbone nicks, typically on one strand. The nanoswitch may be formed in a number of ways, as described in Published PCT Applications WO2013/067489, WO2017/003950, WO2017/139409, WO2017/165585 and WO2017/165647, and such methods are incorporated by reference herein. The analyte-binding agents are typically bound to the nucleic acid at double stranded regions. One exemplary but non-limiting way of making a nanoswitch is to conjugate each of the analyte-binding agents to an oligonucleotide that is complementary to two regions on a nucleic acid (e.g., DNA) scaffold. Each oligonucleotide is then hybridized to the scaffold, thereby placing the analyte-binding agent at the desired location along the length of the scaffold. The remainder of the length of the scaffold may be single-stranded or double-stranded. Specifics relating to nanoswitches are provided in greater detail below.

The approaches described herein use a nanoswitch engineered to undergo a conformational change upon binding of a target analyte. Typically, at least two analyte-binding agents (probes) having the same analyte specificity, for example two antibodies specific for the same analyte, are individually coupled to two specific locations on a nucleic acid scaffold, for example a DNA scaffold. Upon binding of the probes to their respective analyte, the nucleic acid adopts a looped conformation (FIG. 1A). The creation of the loop effectively reduces the length of the nanoswitch as compared to a nanoswitch that has not bound to its respective analyte. The presence of a shorter nanoswitch is therefore indicative of the presence of the analyte. Nanoswitches bound to analytes and thus in the looped conformation may be referred to herein as closed nanoswitches. Nanoswitches not bound to analytes and thus is an unlooped (or linear) conformation may be referred to herein as open nanoswitches. As described in greater detail herein, the nanoswitch may be any length provided the end user is able to observe and distinguish between open and closed conformations. Certain exemplary and thus non-limiting nanoswitches of about 7 kbp in length are described in the Examples.

Nanoswitches of this disclosure have several advantages over conventional techniques. First, the majority of current methods use surfaces to detect molecules by capturing analytes, but surfaces are highly susceptible to non-specific binding that causes a high false-positive background. DNA nanoswitches capture the target analytes in solution, eliminating the need for surfaces. Second, rather than waiting for the target analyte to bind to the surface-immobilized analyte-binding probe such as an antibody, a high concentration of nanoswitches in solution can rapidly collide with and capture the target analytes. Third, having both analyte-binding probes (e.g., antibodies) on the same nucleic acid construct increases the overall association equilibrium of the probes to the analyte. The analyte has to dissociate from both probes in order to dissociate from the nanoswitch, and once the analyte is bound to one of the probes, the other probe will be in close proximity to and rapidly bind the analyte.

After incubating a sample with the nanoswitches for a time and under conditions sufficient to capture the target analytes, the next step is to quantify looped nanoswitches to determine the amount of target in the sample. This has been done using gel-electrophoresis. In this way, the looped nanoswitches migrate in the gel more slowly than the linear nanoswitches, separating themselves into a distinct band with an intensity that corresponds to the amount of analyte in the sample (FIG. 1B). This was recently demonstrated in a nanoswitch-linked immunosorbent assay (NLISA) that achieved fM level sensitivity in biological samples [13]. The lower detection limit of gel-based readout is restricted to ~10 fM, due to auto-fluorescence of the gel and the sensitivity of the gel-imager. The single-molecule approaches described herein can overcome this signal integration issue typically associated with bulk-ensemble methods.

A more thorough discussion of nanoswitches is provided below.

Force-Controlled Immunoassay (FCI)

Force-controlled immunoassay (FCI) is a novel detection platform that combines solution-based analyte binding with force-controlled single molecule techniques. Using this platform, detection of prostate specific antigen (PSA) of single-digit attomolar concentrations was possible, as described in the Examples. This low limit of detection was achieved by increasing the number of analyte-binding probes by many orders of magnitude (e.g. by over $10^9$ fold) compared to standard single-molecule force experiments. Nucleic acid nanoswitches (NS) were used as analyte-binding probes. These undergo a conformational change as a result of binding to their intended biomarker (referred to herein as an analyte), thereby registering as an "on" or "closed" signal. The conformational change is associated with a change in length which can be efficiently read-out by a parallel stretching of a plurality (e.g., thousands) of surface-tethered nanoswitches in a microfluidic channel. The nanoswitches may be stretched, for example, by applying a force on a microsphere attached to the free end of the nanoswitch. One such suitable force is induced using hydrodynamic flow (see FIG. 1C).

The nanoswitches of this method are functionalized on both ends. The first end is functionalized to bind to a surface, such as but not limited to a flow cell surface, or a microscope slide surface. This end may be modified in virtually any way. Typically, it is conjugated to a first member of a binding pair and the intended surface has conjugated to it the second member of the same binding pair. An example of a suitable binding pair is the digoxigenin (Dig) and anti-Dig antibody binding pair. This binding pair is used in the Examples to tether a nanoswitch to a surface. Other binding pairs including other antigen-antibody binding pairs may be used. The second end is functionalized to bind to a detectable moiety such as a bead. The detectable moiety may serve a variety of purposes. First, it may be used to detect the nanoswitch, visualize its trajectory, measure nanoswitch length and/or detect a rupture event. This is illustrated in FIG. 1C. Second, it may be used to isolate nanoswitches during the method. This is illustrated in FIG. 1E in which the moiety is a magnetic bead. In some instances, the detectable moiety is a fluorescently labeled magnetic bead. Third, it may provide a means for applying force to the nanoswitch, thereby enabling the stretching of the nanoswitch and/or rupture of the non-covalent bonds that create the looped nanoswitch. The second end of the nanoswitch may also be conjugated to a first member of a binding pair and the detectable moiety is conjugated to the second member of a binding pair. An example of a suitable binding pair is a biotin-avidin (e.g., streptavidin) binding pair. This binding pair is used in the Examples to tether the nanoswitch to a bead. The nanoswitch may be biotinylated and the bead may comprise avidin (e.g., streptavidin) on its surface. Beads may comprise more than one avidin moiety and thus may bind more than one nanoswitch. Methods for identifying beads tethered to a single nanoswitch are provided herein. It is to be understood that the modifications at the first and second ends of the nanoswitches are different from each other and also different from the analyte-binding agents that are present on the nanoswitch.

The optical read-out can be performed with standard optical microscopy in bright field, without the need for any labeling of the nanoswitch or any specialized instrumentation. However, it is to be understood that the nanoswitch may also be visualized by labeling the nanoswitch itself (e.g., using a nucleic acid stain) or by labeling the end-conjugated bead, in the event the bead is not itself detectable (i.e., if the bead is non-magnetic and/or non-fluorescent). Using this approach, more than a thousand trajectories can be recorded in parallel revealing several hundreds of verified single molecule experiments recorded in one frame (see FIG. 1D). Due to the design of the setup, the focus can be moved along the flow cell, multiplying the number of investigated beads by the number of scanned frames. By scanning the whole flow chamber, more than 5000 verified single-molecule experiments have been obtained in one experiment with a duration of 10 minutes. The ability to analyze hundreds or thousands of nanoswitches in a short period of time is useful when rare analytes are being detected.

The assay, which may be referred to herein as the Force-Controlled Immunoassay (FCI)/Lateral Force Microscope (LFM), may be performed in two different modes: constant force or dynamic force. In constant force measurements, a constant flow is applied and the tether length is monitored revealing the conformation of the nanoswitch (see FIG. 1E. Subsequently, a reverse flow is applied for checking the symmetry of the trajectory in order to verify the single-molecule nature of the analysis. Using this approach, the nanoswitches bound to analytes may be enriched using sequence-specific endonucleases, as described herein. In dynamic force measurements, the hydrodynamic flow rate is increased revealing the force-extension curve of the DNA tether. The hydrodynamic force may be increased linearly or it may be increased in a non-linear manner. As provided herein, the dynamic force mode enables massive parallel force spectroscopy of single molecules.

Sensitivity. The FCI/LFM method, like the nucleic acid curtain method discussed below, may be used to detect rare analytes, including rare analytes in small volume samples. As evidenced in the Examples, the FCI/LFM method has demonstrated a limit of detection of 1.2 attomolar (aM) from a 100 microliter (uL) sample volume for the PSA protein. A 100 uL aliquot of a sample having an analyte at a 1.2 aM concentration contains about 72 such analytes, and the FCI/LFM method is able to detect 1 out of those 72 target molecules.

Single-molecule analysis verification. The method is illustrated in FIG. 1C which shows a nanoswitch attached at a first end to a surface, such as a microfluidic flow cell surface, and attached to its second untethered end a detectable moiety. The detectable moiety may be used to visualize the nanoswitch and/or to isolate the nanoswitch as described herein and as shown in FIG. 1F. In FIG. 1C, the nanoswitch is detected via the detectable moiety on its untethered end. In the bottom left configuration, the nanoswitch is not bound to an analyte and the Figure illustrates the movement of the nanoswitch (via the position of the detectable moiety) in its open conformation under forward and reverse flow. In the bottom right configuration, the nanoswitch is bound to an analyte and the Figure illustrates that the movement of the nanoswitch in its closed conformation under forward and reverse flow. The maximum distance that the open nanoswitch can travel through both forward and reverse flow is 2 times $(l_o+r)$ where $l_o$ is the length of the open nanoswitch and r is the radius of the detectable moiety. The maximum distance the closed nanoswitch can travel through both forward and reverse flow is 2 times $(l_c+r)$ where $l_c$ is the length of the closed nanoswitch and r is the radius of the detectable moiety. Overall symmetry of the nanoswitch trajectory under forward and reverse flow confirms that the detectable moiety is conjugated to a single nanoswitch, and thus that any prior or subsequent readout using this nanoswitch reflects a single nanoswitch and a single analyte. As will become apparent herein, particularly with reference to FIG. 1F, it is possible that any given detectable moiety (e.g., magnetic bead) is conjugated to more than one nanoswitch, and such "events" should be removed from the dataset as not representative of single-molecules. Thus, in some embodiments, each surface-tethered nanoswitch is interrogated using forward and reverse flow. This may be done in a constant force mode, in which case the trajectory of the nanoswitch is first tracked under forward flow and then again under reverse flow. Symmetrical forward and reverse trajectories represent detectable moieties (e.g., beads) conjugated to single nanoswitches. These are further analyzed with respect to their length and/or rupture force. The nanoswitches and their trajectories may be visualized throughout their length (e.g., if they are stained with a nucleic acid backbone stain) or by their end (e.g., if they are conjugated to a detectable bead at their free, untethered, end).

To include only single-tethered particles into the analysis, the symmetry, s, of each trajectory in retrograde flow was analyzed. The symmetry factor, S, equals $X_1/X_2$ where $X_1$ is the X-displacement during forward flow into the chamber or cell (or during the infusion cycle) and $X_2$ is the X-displacement during reverse flow (or during the withdrawal cycle). For an ideal single tethered bead (i.e., in the context of this disclosure, a bead that is conjugated to a single nanoswitch), the X-displacement in both directions is identical and the symmetry factor, S, is 1. However, there is always an uncertainty in the zero-position due to the Brownian motion of tethered beads. This uncertainty is reflected in the standard error of the mean during the 25 seconds prior to every measurement when no flow is applied. Thus, in some instances, only those trajectories with a symmetry factor differing less than the standard error of the mean from 1 are typically counted as single tethers and included in further analysis. That is, if the S value is 1+/−SEM, then the bead is considered to be conjugated to a single nanoswitch.

In other instances, symmetrical trajectories may be defined as having an $S=X_1/X_2$ that is between 1+/−Epsilon, where Epsilon is chosen to minimize false positive and false negative signals, and is a function of the measurement error. For example, Epsilon could be chosen as the relative SEM under no force.

Alternatively, a tether is symmetrical if asym=(X1−X2)/((X1+X2)/2) is less than Epsilon, where Epsilon is chosen to minimize false positive and false negative signals, and is a function of the measurement error.

Enrichment of closed nanoswitches. The LCI/LFM method may also include an additional step designed to enrich for nanoswitches bound to analytes. This is particularly useful when detecting rare analytes since an excess of nanoswitches should be used and the majority of the nanoswitches will remain in a linear conformation in which case it may be difficult to observe closed nanoswitches in the great excess of linear nanoswitches. To enrich closed nanoswitches, the nanoswitches may be designed such that open nanoswitches are to be cleaved by one or more sequence-specific endonucleases and then resulting fragments removed from the mixture or rendered unable to bind to the surface. This approach is illustrated in FIG. 1F. Other approaches involve designing the nanoswitches such that the open nanoswitches are preferentially degraded, removed or rendered incapable of binding to a surface. For example, other means of cleaving open and closed nanoswitches could be implemented, such as using toehold-mediated strand displacement to remove an oligonucleotide that is bridging a nick (which could be introduced into the scaffold using a nicking restriction enzyme), or using a reducing agent to break one or more disulfide bonds that are holding the nanoswitch together.

The nanoswitches are first contacted in solution (and in an surface-untethered conformation) with sample and allowed to bind to their respective analytes, if present. The concentration of the nanoswitches is typically in vast excess of the concentration of the analyte. Typically, if the analyte is present at a concentration above 10 fM, then nanoswitch concentrations on or about 1.5 nM (e.g., 0.5 through to 2.5 nM, or 0.5 nM, 1.0 nM, 1.5 nM, 2.0 nM, or 2.5 nM) are used. If however the analyte concentration is expected to be less than 10 fM, then nanoswitch concentration may also be lower, including on or about 150 pM (e.g., 50-250 pM, or 50 pM, 100 pM, 150 pM, 200 pM, or 250 pM). Thus, the concentration of nanoswitches may be set to be $10^3$ through to $10^5$ more than the expected concentration of the desired analyte, in some instances.

Incubation times may also vary depending on expected analyte concentration. Samples having analyte concentrations above 10 fM may be incubated with sample for a period of time on the order of a few hours (e.g., 1-2.5 hours, or 1 hour, 1.5 hours, 2 hours, or 2.5 hours), while samples having analyte concentrations less than 10 fM may be incubated for longer periods of time (e.g., 10-15 hours, or 10 hours, 11 hours, 12 hours, 13 hours, or 14 hours).

Virtually any sequence-specific endonuclease (e.g., restriction enzyme) or combination of sequence-specific endonucleases may be used to cut the nanoswitch in the looped region. It is important that the cleavage sites occur in the looped region because cleavage at that location impacts the open and closed nanoswitches differently. The open nanoswitch is cleaved into two nanoswitch fragments one of which will be washed away and thus incapable of binding to the surface in a later step. The closed nanoswitch when cleaved at a similar site remains intact by virtue of the bound analyte. Importantly, the two ends remain complexed together and the nanoswitch can then be tethered to the surface in the later step. The nucleotide sequence of the looped region of the nanoswitch will dictate which endonuclease or which combination of endonucleases can be used in this step. The nanoswitch may be engineered to have particular sequences in some instances. Examples of sequence-specific endonucleases that can be used include but are not limited to AfeI and AlwI, both available from New England Biolabs (NEB).

Following incubation with the sequence-specific endonuclease(s), the mixture is further incubated with a detectable bead such as a magnetic bead which binds to one end of the nanoswitches. Nanoswitches and nanoswitch fragments bound to magnetic beads can then be isolated from the remainder of the mixture and then placed into contact with a surface. As should be apparent from FIG. 1F, only closed nanoswitches are able to bind to the surface because they still retain the end that is needed to binding to the surface. The nanoswitch fragments that result from the cleavage of linear nanoswitches are either washed away or are not able to bind to the surface. This effectively enriches the number of closed nanoswitches bound to the surface. This is important because fewer nanoswitches and thus less surface area must be analyzed in order to detect rare analytes.

It has been found that in some instances a percentage of the linear nanoswitches are not cleaved and thus remain in the mixture and are subsequently tethered to the surface and detected. Provided these "cleavage-resistant" nanoswitches are not so numerous to outcompete the closed nanoswitches for binding to beads or for binding to the surface, they can be ignored and/or used as internal controls for nanoswitch sizing purposes. The bimodal distribution that may be observed is shown in FIG. 4A, which shows a peak at about 1.5 um which represents closed nanoswitches and a peak at about 2.5 um which represents remaining linear nanoswitches.

In some embodiments, in view of the nucleic acid nature of the nanoswitches, EDTA may be added to the mixture before and/or after the cleavage step in order to prevent unwanted degradation of the nanoswitches. This is particularly helpful if the sample may comprise a nuclease (e.g., a serum sample). EDTA may be used at concentrations ranging from 20-500 mM, 50-250 mM, 50-150 mM, or about 100 mM.

Notably our preparation of tethered beads allows us to capture a much higher percentage of analyte than previous tethered-bead, immune sandwich assays (Silver et al. 2015). This is in part due to that when attaching the beads to the surface through tethers in the presence of only a small amount of analyte, our procedure has the small number of tethers activated to the analyte attaching to a surface or bead with binding site without tethers. This is in converse to activating a surface with a small number of analyte, and then trying to bind to another surface or bead that has an excess of tethers, which is unable to sufficiently bind in a rapid fashion. Additionally in our procedure almost all analytes can first be bound with the nanoswitches, which can then be attached to beads before removing excess unbound ends via cleavage, and binding the beads with tethers to the surface, instead of binding beads to a surface that already contains an excess of tethers. Our invention also includes slight variations on our technique to prepare the beads with tethers for attachment to a surface with a high analyte capture ratio. This includes but is not limited to, having two different partial tethers bind to the analyte in solution. After attachment to the beads or surface, excess unbound tethers are washed away before binding the beads to the surface, similar to with the nanoswitches except without requiring a cleavage step. Another variation has single tethers on beads bind to analyte, and then excess sample is washed away and the tether-bound analyte then binds to a surface that has been modified with a sandwiching antibody. Another variation has single tethers on beads bind to analyte, and then excess sample is washed away, either in the initial capture step, or after excess sample has been washed away, a sandwiching antibody is added to bind to the free or tether bound analyte, and after washing the tether-bound analyte sandwiched with an additional antibody then binds to a surface that has been modified to bind to a chemical group on the sandwiching antibody.

Constant and dynamic force analyses. Once the nanoswitches are tethered to a surface, they may be subject to a constant or a dynamic force and the length of the nanoswitch may be measured and/or the force at which a rupture event occurs may be measured. As used herein, a rupture force is the force at which one of the bonds between the analyte and one of the analyte-binding agents breaks. Usually, this bond will be the weaker of the two bonds holding the analyte to the nanoswitch.

In an exemplary method, the nanoswitch is tethered to a surface of interest and then subjected to a constant, relatively lower force that is sufficient to stretch out the nanoswitch but not great enough to cause a rupture event. Such constant force is applied first in a forward direction and then in the reverse direction and the symmetry of the forward and reverse trajectories is determined. Tethers associated with symmetrical trajectories are then further analyzed and/or those not associated with symmetrical trajectories are filtered out of the dataset. The nanoswitches may then be further interrogated using a constant force or a dynamic force. In a constant force setting, a set force is applied to the nanoswitches and their respective lengths are determined. The nanoswitch lengths may distribute somewhat bimodally with a first peak representing the shorter closed nanoswitch conformation and the second peak representing the longer linear nanoswitch conformation.

The amount of force needed may be determined by analyzing the nanoswitch in the absence of any analyte. It is possible that the nanoswitches may manifest a degree of non-specific internal binding leading to false positive counts in the absence of the analyte. This is shown in FIG. 3B which demonstrates non-specific interactions observed at lower pulling forces decrease as the pulling force increases. A suitable pulling force may therefore be set at or around the force at which the false positive rate is nearly zero, again as shown in FIG. 3B. Using a pulling force that is much greater risks rupturing the bond between the nanoswitch and the surface, thereby causing loss of the nanoswitch altogether. The end user must determine empirically the force, and the optimal time to apply this force, that achieves the maximum number of surface-tethered nanoswitches and lowest false positive rate. It will be understood that for longer periods of time, lower optimal force is needed. As shown in the Examples, nanoswitches tethered to a surface using the Dig-anti-Dig binding pair and designed to detect PSA using anti-PSA antibodies are best analyzed at a force of about 6.5 pN held for about 5 seconds. In some instances, the force may be present in a range of about 5.5 pN to about 6.5 pN.

Still another analysis that may be performed involves the use of dynamic force. An increasing force is applied to the nanoswitches which then undergo rupture and re-association events. These rupture events occur at a particular force which is indicative of the analyte bound by the nanoswitch. The number of rupture events occurring as a function of applied force is then plotted as illustrated in FIG. 5A.

Forces. This disclosure provides methods that require the application of force to tethered nanoswitches. The Examples and much of the discussion provided herein refers to hydrodynamic force but it is to be understood that the methods are not so limited. Other forces that may be used include but are not limited to centrifugal force and magnetic force.

Samples. The FCI/LFM methods used herein may be performed on virtually any sample including but not limited to complex biological samples such as whole blood and serum samples.

Multiplexing. It will be understood that the method is amenable to the detection of various analytes simultaneously or concurrently. If done simultaneously, a mixture of nanoswitches may be used each of which binds to a single analyte and then converts itself into a closed nanoswitch having a unique length indicative of that analyte. These nanoswitches may differ from each other in the placement of their respective analyte-binding agents so that nanoswitches that detect a first analyte form a loop of a first size and nanoswitches that detect a second analyte form a loop of the second size that is different and discernable from the loop of the first size. Alternatively or in addition, nanoswitches that bind to different analytes may be distinguished from each other using fluorophores. These could be arranged to form a barcode to enable a large number of different combinations from a smaller number of different colors. DNA sequences may also be used to distinguish between different nanoswitches. For example, each antibody could be coupled to an oligonucleotide that has a common region, designed for example to complement the M13 scaffold, and a unique barcoding region. The barcoding region may be readout using toehold-mediated strand displacement, i.e. after the beads are tethered to the surface by closed nanoswitches, a displacement oligonucleotide is flowed into the chamber with a toehold sequence that matches the barcode, and the nanoswitch will open (or rupture if the nanoswitch has been previously cut). By flowing in a variety of different displacement oligonucleotides sequentially, the identify of each nanoswitch can be determined. These different barcoding methods (loop size, fluorescence, strand displacement) can be combined to increase the number of possible combinations.

Alternatively, the same nanoswitches may be used to detect and/or measure different analytes in sequence. This may be accomplished by removing the pair of analyte-binding agents from a nanoswitch and replacing them with a pair of analyte-binding agents for a new analyte. This may occur by displacing oligonucleotides to which the analyte-binding agents are conjugated, for example using strand displacement, and hybridizing other oligonucleotides conjugated to different analyte-binding agents. Each of the oligonucleotides may have a single-stranded toehold sequence to which a new oligonucleotide may bind and thereby cause displacement. The toehold sequences may be unique for each position in the nanoswitch.

Mechanical Proofreading. The nanoswitches may be used to detect association and optionally dissociation between an analyte and one or both of the analyte-binding agents situated on the nanoswitch. Association of an analyte and an analyte-binding agent is evidenced by the presence of closed nanoswitches which have a characteristic (and thus typically known) length. The nanoswitches may be engineered to provide internal verification that any change in configuration, whether from open to closed or from closed to open, is associated with the interaction between an analyte and its analyte-binding agent(s). This may be accomplished in various ways. One exemplary embodiment is as follows: assume a nanoswitch that comprises a scaffold and a first and a second oligonucleotide, wherein the first and the second oligonucleotides are coupled respectively to the first and second analyte-binding agents. Upon binding of the analyte to its first and second analyte-binding agents, the nanoswitch adopts a closed conformation. Under a certain force, the analyte may dissociate from its analyte-binding agent. However, at lesser forces, the analyte may remain associated with its analyte-binding agent but the oligonucleotide to which the analyte-binding agent may dissociate from the scaffold. This latter form of dissociation, which can be engineered to rupture at a pre-defined force, can also be used to detect the presence, and optionally nature, of the analyte. Dissociation of the oligonucleotide from the scaffold occurs at the pre-defined force only if the analyte is bound. If the analyte is not bound, then the oligonucleotide remains bound to the scaffold even at the pre-defined force. The force required to dissociate the oligonucleotide from the scaffold in a closed nanoswitch, when the analyte is appropriately bound, may be determined a priori. Therefore any observed changes in length that occur at or about this force are internally validating (i.e., they evidence that the analyte is bound to its analyte-binding agents) and can be used to filter true positives from false positives. Such nanoswitches may be used to validate each analyte based on length (or change in length) of the nanoswitch and on the force required to convert the closed nanoswitch to an open configuration. This reduces background noise and false-positive signals.

Also contemplated is the ability to alter and thus customize nanoswitches for particular analytes. For example, the oligonucleotide to which the analyte-binding agent is bound may be modified in length and/or nucleotide composition in order to vary the force at which is dissociates from the scaffold. Longer, GC-rich oligonucleotides will require a higher force to dissociate than will shorter, AT-rich oligonucleotides. The ability to customize and thus distinguish nanoswitches from each other based on behavior in the presence of analyte and under various forces enables multiplexing (i.e., the ability to detect more than one analyte in a sample using a mixture of distinct nanoswitches).

Additional Geometries

This disclosure contemplates additional single molecule length and force measurement strategies. In one such strategy, a sample is contacted with a first analyte-binding agent in solution under conditions sufficient for an analyte, if present in the sample, to bind to the first analyte-binding agent. The first analyte-binding agent is typically coupled to a detectable moiety such as a bead. The resulting mixture is then contacted with a surface-tethered second analyte-binding agent. The first and second analyte-binding agents may be identical or they may be different, as described herein.

The resultant complex is surface-tethered and comprises an analyte bound to two analyte-binding agents an coupled to a bead. It can be individually interrogated using force-controlled immunoassay strategy described herein.

A representative complex is shown in FIG. 1I and its analysis may be carried out as shown in FIG. 1J. The complex may be optionally interrogated as shown in FIGS. 1C and 1E and accordingly the method may also involve analyzing whether the complex has an expected trajectory in flow, again as shown in these Figures.

The length of the complex, under force, can be used to identify the analyte, since the complexes and their components may be engineered to have a characteristic length for particular analytes, as shown in FIG. 1H.

In addition to using force to stretch out the complex, and thereby measure its length, it may also be used to rupture the complex as illustrated in FIG. 1J. Unlike FIGS. 1C and 1E, the rupture will result in a loss of the bead altogether rather than simply a lengthening of the complex. Nevertheless, the force at which such rupture occurs can be used as an internal validation of the identity of the analyte bound to the complex.

The bead may be coupled to the first agent directly or via a linker (also referred to herein as a tether) such as but not limited to a nucleic acid, whether single-stranded, double-stranded or partially double-stranded (also referred to as a partial duplex). For example, in some instances, the bead may be coupled to a first nucleic acid, of known and defined length, and the first agent may be coupled to a second nucleic acid, also of known and defined length. The first and second nucleic acids hybridize to each other to couple the agent to the bead at a known and defined length.

An illustration of an exemplary functionalized bead is provided in FIG. 1G. right most panel. The conformation of the nucleic acids and first agent is notable as it allows tuning of the force that is required to rupture the nucleic acid duplex. In other words, positioning the analyte-binding agent such that it is bound at the interface of the single and double stranded regions, and not at the free end of the nucleic acid tether, provides certain advantages, including for example the ability to fine-tune the force that is required to disrupt the duplex.

The tethers that couple the bead to the first agent may be a scaffold nucleic acid (e.g., M13) hybridized to one or more oligonucleotides. One terminal oligonucleotide may be conjugated to biotin and the other terminal oligonucleotide may be conjugated to the first agent, as an example. The bead may be conjugated to avidin such as streptavidin.

Similarly, the surface may be coupled to the second agent directly or via a linker such as but not limited to a nucleic acid, whether single-stranded, double-stranded or partially double-stranded. For example, in some instances, the surface may be coupled to a first nucleic acid, of known and defined length, and the second agent may be coupled to a second nucleic acid, also of known and defined length. The first and second nucleic acids hybridize to each other to couple the agent to the surface at a known and defined length.

The tethers that couple the first agent to the surface may also be a scaffold nucleic acid (e.g., M13) hybridized to one or more oligonucleotides. One oligonucleotide, such as a terminal oligonucleotide, may be conjugated to digoxigenin and another oligonucleotide, such as the other terminal oligonucleotide, may be conjugated to the second agent, as an example. The surface may be conjugated to anti-digoxigenin.

As discussed above, this strategy provides an mechanical proofreading strategy as described herein that internally validates the presence and identity of the analyte. Specifically, the hybridization event that couples the bead to the first agent may be engineered to rupture at a particular, pre-defined force by varying the length and/or nucleotide composition of the tethering nucleic acids. Only rupture events that occur at or near this pre-defined force will be considered true positives and thus monitored. The ability to filter events in this manner allows an end user to reduce false positives and thus background.

In an alternative embodiment, the hybridization event that couples the second analyte-binding agent to the surface may be engineered to rupture at a particular, pre-defined force by varying the length and/or nucleotide composition of the tethering nucleic acids. In this instance, the tether that couples the bead to the first analyte-binding agent may be lengthened.

The distance between the surface and the bead (referred to herein as the length of the complex) can also be used to filter true positives from false positives. Such distance can be customized by varying the length of the tether that couples one of the analyte-binding agents to the surface and/or by varying the length of the tether that couples the bead to the other analyte-binding agent.

The force to be applied may be dynamic (e.g., increasing) or it may be constant. If the latter, then complex lifetime (i.e., the time it takes for the complex to rupture under a constant force) may be measured in place of rupture force. Additionally, the force may be but is not limited to hydrodynamic force, magnetic force or electrical force.

Thus, length of the complex under force in the absence of complex rupture and/or force at which the complex ruptures (e.g., the dissociation of the tethered bead from the first analyte-binding agent, as illustrated in FIG. 1J) and/or the lifetime of the complex under constant force (e.g., the time it takes for the bead to dissociate from the first analyte-binding agent, as illustrated in FIG. 1J) can be used individually or as a combination to distinguish true positives from false positives. One, two or all three of these pre-defined characteristics may be used.

Nanoswitch Curtains

The nanoswitch curtain assay involves a single-molecule approach and has several technological advantages over digital-ELISA to further increase the sensitivity limit to single-digit attomolar (aM, ~60 molecules in a 100-μL sample), which enables numerous applications requiring protein detection including infectious disease detection and health screening.

Achieving high-sensitivity requires in part the ability to interrogate a large number of DNA nanoswitches (~one million) to determine whether they are looped or not. The looped vs. linear conformations can be distinguished by measuring the end-to-end extension since the looped construct is shorter than the linear construct. The nanoswitch curtains technique facilitates making such measurements with speed and accuracy.

The DNA curtains technique was developed in the field of single-molecule biophysics to enable massively parallel data collection of protein-DNA interactions [19, 20]. Nanofabricated structures (metallic "nanobarriers") are used in combination with a lipid bilayer surface to align multiple extended nucleic acids into a curtain-like pattern in the presence of flow (FIG. 6A). The lipid-tethered nucleic acids can move across the lipid bilayer surface in the direction of the applied hydrodynamic force until they are halted by the nanobarrier, causing them to accumulate and extend across the imaging plane. With an array of nanobarriers, up to a million nanoswitches can be imaged in one microfluidic channel [20]. To incorporate the nanoswitch into the curtain, one end of the nanoswitch is functionalized (e.g., biotinylated) so it can tether to a moiety in the lipid bilayer such as a lipid-functionalized streptavidin. The other end of the nanoswitch is also functionalized through attachment to a visible and/or weighted moiety such as a particle, a dye, or a quantum-dot. This latter moiety is used to extend and/or visualize the nanoswitch, including the end of the nanoswitch, and thus to measure its end-by-end extension by imaging (FIG. 6B).

The method also provides multiplexing capability (i.e., the ability to detect multiple analytes from the same sample). This facilitates biomarker and pathogen profiling. The modularity of nanoswitches can be used to make a library that consists of different nanoswitches to target multiple analytes. Specifically, nanoswitches of different sized loops can be designed that uniquely correspond to different analytes by varying the locations of the two analyte-binding agents. Additionally, differently colored fluorophores can be used for multiplexing. The nanoswitch can be engineered to detect DNA/RNA molecules by having oligonucleotides that are complementary to the sequence of interest as the analyte-binding agents [21].

An exemplary assay scheme, taking on the order of about 30 minutes, is illustrated in FIG. 7 and is as follows:
(1) 20 minutes of nanoswitch incubation in the sample (sufficient to capture nearly all the target analytes if the nanoswitch is at a higher concentration than the analyte or at least ~1 nM.)
(2) 5-10 minutes of incubation within the microfluidic channel containing the lipid bilayer will sufficiently tether one million nanoswitches to the lipid bilayer surface with the biotin-streptavidin linkage.
(3) Image the nanoswitch curtains under flow with a conventional fluorescent microscope, followed by an automated analysis software that counts individual target analytes by the extension and colors of the signal.

This aspect of this disclosure provides, inter alia, a product comprising (a) a solid support, (b) a plurality of lipids capable of forming a fluid lipid bilayer that can be disposed on the solid support, and (c) a plurality of nanoswitches. The components of such product may be arranged such that the plurality of lipids forms the fluid lipid bilayer that is disposed on the solid support or is provided in a separate housing. Similarly, the plurality of nanoswitches may be inserted in the fluid lipid bilayer or may be provided in a separate housing. The support may be glass, fused silica ($SiO_2$), quartz, borosilicate glass, polydimethylsiloxane, polymerized Langmuir Blodgett film, functionalized glass, Si, Ge, GaAs, GaP, $SiO_2$, $SiN_4$, modified silicon, or a polymer (e.g., (poly)tetrafluoroethylene, (poly)vinylidenedifluoride, polystyrene, or polycarbonate). The support may be or may comprise fused silica. The support can be virtually any shape or volume such as for example a disc, square, rectangle, sphere or circle. The support may be a slide used for fluorescent microscopy.

Disposed on the support may be a coating material such as for example lipids, a lipid layer, a lipid bilayer, a fluid lipid bilayer, etc. In one embodiment, the lipids are zwitterionic lipids. In one embodiment, polyethylene glycol (PEG) is added to the lipid bilayer. For example, 1%, 2%, 3%, 4%, 5%, 6%, 7%, 8%, 9%, 10%, 12% (w/w) or more of PEG can be included in the lipid bilayer.

The support may be designed to accommodate any number of nanoswitches including for example 50, 100, 250, 500, 1000, 2000, 5000 $10^4$, $10^5$, $10^6$, $10^7$, or more nanoswitches. The number of nanoswitches that may be attached to the support may vary depending on the size of the support and by the design of the array.

The nanoswitches may be coupled or bound or stained with a label such as a fluorescent label. Such labels include but are not limited to nucleic acid stains such as YOYO1 (Molecular Probe, Eugene, Oreg.), TOTO1, TO-PRO, acridine orange, DAPI and ethidium bromide, and fluorescent particles such as quantum dots.

The nanoswitches may be conjugated to a lipid on a first end and a particle on a second end. Alternatively, the nanoswitches may comprise on a first end a first member of a binding pair and a lipid in the bilayer may comprise the second member of the binding pair. Thus, the nanoswitches become attached to the bilayer through the covalent or noncovalent interaction between the first and second members of the binding pair. One example of such a binding pair is a biotin and avidin binding pair. Reference to avidin herein intends avidin and variants thereof having binding affinity for biotin, including streptavidin and neutravidin.

The nanoswitches may be provided with a particle conjugated to a second end, or the particle may be attached during the process. Either way, the particle may be conjugated to the nanoswitch using covalent or noncovalent means including use of a binding pair such as an antigen-antibody binding pair or a biotin-avidin binding pair. As should be clear, the binding pair used for conjugation at a first end should be different from the binding pair used for conjugation at the second end. Thus, in some embodiments, the nanoswitches may comprise on a first end a first member of a first binding pair and on a second end a second member of a second binding pair. A lipid in the bilayer may comprise a second member of the first binding pair and a particle may comprise the first member of the second binding pair. Due to the arrangement of lipids in a lipid bilayer, typically the binding member or other functionalization of the lipid will occur in the lipid head group.

The support typically further includes a barrier such as a diffusion barrier. The barrier prevents lipid, and thus nanoswitch movement, beyond a particular region in the bilayer. This serves to align the lipids and thus also the nanoswitches, thereby forming a "curtain" structure. In the case where a single type of nanoswitch is used to detect a rare analyte, most of the detectable nanoswitches will not have bound an analyte and will have a first length, and a small minority of detectable nanoswitches will be bound to an analyte and will have a shorter length. The latter nanoswitches will be apparent, as shown for example in FIG. 6A.

The barrier used to align the nanoswitches may be a mechanical barrier, a chemical barrier, or a protein barrier. A mechanical barrier may be for example a scratch or etch on the support. A protein barrier may be for example a deposition of protein, such as but not limited to fibronectin, at specific regions on the support. A chemical barrier may be for example one or more metals, such as chromium, aluminum, gold, titanium, platinum, osmium, or nickel deposited on the support. Chemical barriers may comprise metal oxides, such as aluminum oxide, titanium oxide, etc. deposited on the support. Any of these barriers may have a thickness of 2, 3, 4, 5, 6, 7, 8, 9, 10, 15, 20 microns and may be arranged for example as shown in FIG. 6A, although not so limited.

In some embodiments, the nanoswitches may comprise a first member of a binding pair and the barrier may comprise a second member of the binding pair. Once the nanoswitches are moved into close proximity with the barrier, for example by hydrodynamic force, the first and second members of the binding pair may associate thereby conjugating the nanoswitch to the barrier. This interaction may serve to align the nanoswitches as well.

The various aspects provided herein may involve use of a cell, such as a flow cell including a microfluidic flow cell. The supports and surfaces described herein for holding and/or tethering nanoswitches may be placed into such cells or they may be an integral part of the cell. Such flow cells typically include two openings, for example an inlet port and an outlet port. The cell may include a cover such as for example a glass cover or a glass coverslip, which optionally may be adhesively attached at its perimeter to the support, creating a chamber between the support and the cover. The inlet port and the outlet port open into the chamber, allowing the application of a hydrodynamic force into the chamber.

To be visualized, the nanoswitches may be exposed to a light source such as for example a laser, at the excitation wavelength of the particular fluorescent label or stain present on the nanoswitch and the resulting fluorescence at the emission wavelength detected. Detection of the emitted fluorescence may use a microscope such as a fluorescent microscope. In another embodiment, excitation and detection is mediated by Total Internal Reflection Fluorescence Microscopy (TIRFM), or other modalities.

Nanoswitch Embodiments

In some embodiments, each nanoswitch is comprised of a scaffold nucleic acid hybridized to a plurality of oligonucleotides. Such nanoswitches may be at least 50%, at least 60%, at least 70%, at least 80%, at least 90%, at least 95%, at least 96%, at least 97%, at least 98%, at least 99%, or 100% double-stranded. In some embodiments, they are at least 80% double stranded. The nanoswitches may therefore comprise double-stranded and single-stranded regions. As used herein, a double-stranded region is a region in which all nucleotides on the scaffold are hybridized to their complementary nucleotides on the oligonucleotide. These double-stranded regions may comprise "single-stranded nicks" as the hybridized oligonucleotides are not ligated to each other. The single-stranded regions are scaffold sequences that are not hybridized to oligonucleotides. The disclosure contemplates the use of nanoswitches having one or more single-stranded regions in between double-stranded regions (typically as a result of unhybridized nucleotides in between adjacent hybridized oligonucleotides). The disclosure further contemplates other nanoswitch forms regardless of their method of manufacture.

In some instances, the nanoswitch is formed by first hybridizing unmodified (or fixed) oligonucleotides to the scaffold nucleic acid to form an intermediate, and then hybridizing modified (or variable) oligonucleotides to the scaffold nucleic acid to form the nanoswitch. The modified oligonucleotides may be combined with (and typically hybridized to) the scaffold simultaneously or sequentially. As used herein, an intermediate refers to a scaffold that is hybridized to some but not the entire complement of oligonucleotides that is designed to bind to the entire length of the scaffold.

The scaffold nucleic acid may be of any length sufficient to allow association (i.e., binding) and dissociation (i.e., unbinding) of analyte-binding agents to occur, to be detected, and to be distinguished from other events. In some instances, the scaffold nucleic acid is at least 1000 nucleotides in length, and it may be as long as 20,000 nucleotides in length (or it may be longer). The scaffold nucleic acid may therefore be 1000-20,000 nucleotides in length, 2000-15,000 nucleotides in length, 5000-12,000 in length, or any range therebetween. The scaffold may be a naturally occurring nucleic acid (e.g., M13 scaffolds such as M13mp18). M13 scaffolds are disclosed by Rothemund 2006 Nature 440:297-302, the teachings of which are incorporated by reference herein. In some embodiments, the scaffold nucleic acid may be at least 150, at least 200, at least 250, at least 300, at least 350, at least 400, at least 450, at least 500, at least 600, at least 700, at least 800, or at least 900 nucleotides in length. The scaffold nucleic acid may therefore be 500-1000 nucleotides in length, without limitation. In some embodiments, the scaffold and oligonucleotides are chosen and the analyte-binding agents are positioned to yield loops of about 40-100 base pairs. The scaffold nucleic acid may also be non-naturally occurring nucleic acids such as polymerase chain reaction (PCR)-generated nucleic acids, rolling circle amplification (RCA)-generated nucleic acids, etc. In some embodiments, the scaffold nucleic acid is rendered at least partially single-stranded either during or post-synthesis. Methods for generating a single-stranded scaffold include asymmetric PCR. Alternatively, double-stranded nucleic acids may be subjected to strand separation techniques in order to obtain the single-stranded scaffold nucleic acids. The scaffold nucleic acid may comprise DNA, RNA, DNA analogs, RNA analogs, or a combination thereof, provided it is able to hybridize in a sequence-specific and non-overlapping manner to the oligonucleotides. In some instances, the scaffold nucleic acid is a DNA.

In some instances the scaffold nucleic acid is hybridized to at least two oligonucleotides, and in some instances to a plurality of oligonucleotides. Each of the plurality of oligonucleotides is able to hybridize to the scaffold nucleic acid in a sequence-specific and non-overlapping manner (i.e., each oligonucleotide hybridizes to a distinct sequence in the scaffold). The nanoswitch may comprise varying lengths of double-stranded regions. As a non-limiting example, 90% or more, including 95%, 96%, 97%, 98%, 99% and 100% of the scaffold nucleic acid may be hybridized to oligonucleotides. It is to be understood that the scaffold may also comprise a plurality of nicks that are typically located between bound oligonucleotides. The length and the number of oligonucleotides used may vary. It will be understood that the greater the length of the oligonucleotides, the fewer that will be needed to hybridize to the scaffold nucleic acid in its entirety. In some instances, the length and sequence of the oligonucleotides is chosen so that each oligonucleotide is bound to the scaffold nucleic acid at a similar strength. This is important if a single condition is used to hybridize a plurality of oligonucleotides to the scaffold nucleic acid. In some instances, the oligonucleotides are designed to be of approximately equal length. The oligonucleotides may be about 10, about 15, about 20, about 30, about 40, about 50, about 60, about 70, about 80, about 90 or about 100 nucleotides in length. The number of oligonucleotides in the plurality may be about 50, about 60, about 70, about 80, about 90, about 100, about 110, about 120, about 130, about 140, about 150, about 160, about 170, about 180, about 190, or about 200, without limitation.

The number of oligonucleotides hybridized to a particular scaffold may vary depending on the application. Accordingly, there may be 2 or more oligonucleotides hybridized to the scaffold, including 3, 4, 5, 6, 7, 8, 9, 10, 20, 30, 40, 50, 60, 70, 80, 90, 100, 200, 300, 400, 500, 600, 700, 800, 900, or 1000 or more oligonucleotides. It will be understood that the number of oligonucleotides will depend in part on the application, the length of the scaffold, and the length of the oligonucleotides themselves.

According to the invention, certain of the oligonucleotides hybridized to the scaffold nucleic acid will be unmodified. The majority of oligonucleotides hybridized to a scaffold nucleic acid may be unmodified. Unmodified oligonucleotides may be referred to herein as "fixed" oligonucleotides.

Other oligonucleotides hybridized to the scaffold may be modified. Modified oligonucleotides include those that are linked to analyte-binding agents such as antibodies or antigen-binding antibody fragments, or those that are linked to first or second members of a binding pair such as a biotin-avidin binding pair, or a Dig—anti-Dig binding pair, etc. These latter types of binding pairs may be used to further functionalize the nanoswitch, for example to conjugate a particle to the nanoswitch or to immobilize the nanoswitch to a surface or to link a nanoswitch to a lipid, etc.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

The following Examples are meant for illustrative purposes, and are not meant to be exclusive or limiting.
Materials and Methods
DNA Nanoswitch Formation DNA nanoswitches with Anti-Digoxigenin and Biotin functionalities were assembled from circular M13mp18 ssDNA (New England Biolabs) as described in Koussa et al. 2015 [12]. The antibodies were first coupled to DNA oligos which were later hybridized onto the DNA scaffold as described in Hansen et al. 2017 [13]. After hybridization, the DNA nanoswitches were purified by using MicroSpin S-400 HR Columns (GE Healthcare, Little Chalfont, GB) and stored at 4° C. Prior to purification the DNA construct was diluted 1:50 in NF free water or 1×PBS buffer. Purification causes a reduction of DNA concentration—check concentration after purification.
Surface Preparation The microscopy slide and cover slip were cleaned with 1 vol. % Helmanex III (Hellma Analytics) diluted in Millipore water. The cover slips were assembled onto a Wash-N-Dry Coverslip Rack from Diversified Biotech (WSDR-1000) and placed into a 100 mL VWR beaker. The glass slides were microwaved in Hemanex III solution for 45 s and sonicating for 20 min. Subsequently, the glass slides were rinsed with Millipore water and dried under moderate stream of Nitrogen gas. The clean glass slides were stored under low pressure in Bel-Art Polycarbonate Vacuum Chamber and the cover slips were functionalized with DNA probes.

The surface functionalization with DNA probes is based on the specific binding between anti-digoxigenin (anti-dig) and Digoxigenin (dig), where digoxigenin is covalently coupled to the DNA construct (see DNA nanoswitch formation). In a three-step process, the cover slips were first coated with nitrocellulose (NC), followed by unspecific adsorption of anti-digoxigenin (anti-dig) which finally couples the dig-functionalized DNA constructs. For preparing stock NC solution, 1% of NC membrane was dissolved in amyl acetate for 30 minutes in a rotator resulting in a concentration of about 10 mg/mL. Then, a 1"×1" square of membrane was cut and weighed, and an appropriate amount of amyl acetate solution was added. The solution was vortexed if the membrane was not completely dissolved. Prior to surface coating, the NC solution was further dissolved to 0.2% (w/w) by diluting 5 µL 1% NC solution into 20 µL of amyl acetate. The cleaned cover glass was coated with 1 µL of 0.2% NC solution. The droplet was placed on one side of the glass slide and was streaked across to the other side, the pipette tip was turned parallel to the glass and the solution was run back and forth on the glass slide until the solution fully covered the slide. Any excess solution on one edge of the glass was left, the slide was placed onto a drying rack with the edge with excess solution pointing downwards so that solution drops off during drying. The drying rack with NC coated cover slips was placed into an oven for a minimum of 5 minutes at 80° C. The surfaces were cooled down and stored at low pressure.

In the second step, the surface was incubated for 20 minutes with 0.05 g/L anti-digoxigenin (11333089001, Roche), diluted in 1×PBS, pH 7.4. After antibody attachment, the channel walls were passivated with 10 mg/mL Western Blocking Reagent in PBS ordered from Sigma Aldrich for 1 hour; the blocking solution was replaced every 15 minutes. Subsequently, the channel was rinsed thoroughly with 80 µL of 1×PBS, pH 7.4. The DNA constructs were first attached to Streptavidin coated Dynabeads MyOne C1 ordered from Thermo Fisher Scientific. The Dynabeads were washed extensively and diluted to a concentration of 1 g/mL in PBS before mixing with DNA constructs, incubated for a minimum of 5 minutes and subsequently introduced into the fluid chamber. A final concentration of less than 2.5 pM DNA construct was chosen to obtain a high bead concentration on the surface with a sufficient spacing of above 2 µm to facilitate as many single tethered beads as possible. After tethering, the chamber was flipped upside down and loose beads were washed out by applying a gentle fluid flow of 2 µL/min.
Assembly of Fluid Cell The design of the fluid cell is kept as simple as possible to provide a cheap disposable device with reduced preparation effort. The fluid cell was prepared from double sided 0.25 mm Kapton tape sandwiched between an anti-digoxigenin functionalized cover slip and a microscopy. The channel was cut into the Kapton tape by using a cut plotter (Graphtec). Two 0.7 mm holes were drilled into the microscopy slide serving as solution inlet and outlet. The tubing was connected to the inlet and outlet via 200 uL Pipette tips gently pushed into the holes.
Flow Cell Measurement All flow cell measurements were performed with a syringe pump (Harvard Apparatus, Holliston, Mass. USA) equipped with a 3 mL syringe (BD Diagnostics). By using a syringe pump, the flow velocity and volume can be precisely controlled which ensures the accuracy of the measurement since the flow velocity determines the force acting on the bead and thus the force acting on the protein-antibody bond. The flow cell enables two different types of experiments: the static force mode and the dynamic force mode, where the latter is similar to a force spectroscopy measurement performed by optical/magnetic tweezer or atomic force microscopy. A 5 MP camera mounted on a standard optical microscope with a 20× magnification was used for recording the movement of surface tethered beads in one field of view.

For determining the tether length, the constant force mode was applied. Prior to every experiment, the zero position of the beads was determined by recording the Brownian motion of the beads for 25 seconds with a sampling rate of 2 fps. Subsequently, flows with rates from 20 uL/minute to 100 uL/minute were applied resulting in forces from 2 pN to 20 pN. A retrograde flow was applied prior to every measurement for identifying single tethered beads. Single tethered beads exhibit a symmetric trajectory when flowing back and forth revealing the same stretching length in both directions (see data analysis for details).

Data Analysis

The digital videos were analyzed by using the open source software ImageJ 1.50i (Wayne Rasband, National Institute of Health, USA) and the ImageJ Plugin "Particle Tracker Classic" written by Sbalzarini and Koumoutsakos [14]. The Particle Tracker Classic provides the x and y positions of each individual bead over time. Due to the design of the device, only the x position is required for obtaining the tether length. The ImageJ software includes all trajectories into a table that was further analyzed by using MATLAB. In MATLAB, all individual trajectories were analyzed regarding their maximum displacement in x direction. To include only single tethered particles into the analysis, the symmetry, s, of each trajectory in retrograde flow was analyzed. The symmetry factor, s, equals $X_1/X_2$ where $X_1$ is the x-displacement during infusion and $X_2$ is the x-displacement during the withdraw cycle. For an ideal single tether, the x-displacement in both direction is exactly identical and the symmetry factor, s, is 1. However, there is always an uncertainty in the zero-position due to the Brownian motion of tethered beads. This uncertainty is reflected in the standard error of the mean during the 25 seconds prior to every measurement when no flow is applied. Only those trajectories with a symmetry factor differing less than the standard error of the mean from 1 were counted as single tethers and included in further analysis. The maximum tether length of the filtered trajectories was included in a histogram and the most probable tether length was obtained from a Gaussian fit to the data.

Force Calibration

Further force calibration was performed by using a zipper construct with the DNA sequence 3'-CTCAAATAT-CAAACCCTCAATCAATATCT-5' (SEQ ID NO: 1). The force that induces unzipping is well known from previous studies [12]. The relationship of flow velocity at rupture and previously determined rupture force was used as a conversion factor in all experiments.

The force acting on the beads is proportional to the flow velocity of the fluid. By increasing the flow velocity, the tether length of linear DNA constructs extends as expected from the Worm Like Chain (WLC) model with a counter length of 2.48 µm and a persistence length of 48 nm [Halvorsen et al. 2011, ref. 7]. By fitting the WLC to the flow-extension curve of the most probable extension of all linear DNA constructs in a field of view, the force acting on the bead can be obtained. The ratio between flow velocity and force provides a calibration factor characteristic for each Flow Cell. The force calibration determined by WLC model corresponds well to the conversion factor found by the zipper calibration.

Sample Preparation 90 uL of the sample was mixed 10 uL of 1.5 nM nanoswitch diluted in PBS, and incubated for 30 minutes to 12 hours, depending on the PSA concentration in the sample. After incubation, the nanoswitch was cut within the looped region by using the cleavage enzymes AfeI and AlwI (New England Biolabs (NEB)). For buffer exchange, the nanoswitches were attached to Dynabeads and washed two times with Cutsmart buffer. The beads were resuspended in 100 uL Cutsmart buffer and 1 uL of each enzyme was added and incubated for 1 hour. Subsequently, the beads were washed twice with 1×PBS buffer to remove the loose nanoswitches. Nanoswitch cleavage significantly reduces the number of beads tethered to linear (open, unbound) nanoswitches and increases the limit of detection by orders of magnitude.

Sample Preparation from Serum and Whole Blood 1 microliter (uL) PSA in different concentrations was spiked into a 9 uL serum or whole blood sample from bovine, then diluted to 50 ul with 1×PBS and mixed with the nanoswitch to a final concentration of 150 pM to 1.5 nM. The nanoswitches were incubated with the sample for 30 minutes to 8 hours, depending on the measurement. Before bead purification, the sample was again diluted with PBS buffer in a ratio 1:1 and the Dynabeads C1 beads were added and incubated for 10 minutes. The beads were washed 6 times with 100 ul washing buffer (1λPBS, 0.2% Tween) and resuspended in 50 ul Cutsmart buffer (New England Biolabs). Subsequently, two cleavage enzymes were added (AfeI and AlwI, New England Biolabs) and the mixture was incubated for 1 hour. After cleavage, closed (bound) nanoswitches were purified with magnetic beads by washing three times with 1×PBS buffer and injected in the flow cell.

Results

The biomarker detection measurements were successfully performed in complex biological fluids using the Force-Controlled Immunoassay (FCI). First, the FCI was force-calibrated using well-understood molecular interactions and the signatures of the nanoswitches were characterized, as a proof of principle. Later, experiments aimed at detecting PSA in serum and whole blood were performed, and ultrasensitive detection was demonstrated.

Force Calibration and Sensitivity Characterization

Prior to sensing applications, the operational force range and nominal sensitivity of the FCI assay was characterized. To calibrate the force acting on the bead, DNA unzipping experiments of a 29 base pair interaction were performed (FIG. 2A). The DNA unzipping force of 14.6 pN was characterized in previous studies using optical tweezer and centrifugal force microscopy [6]. The DNA construct was tethered between the channel wall of the flow cell and a micronbead and performed dynamic force spectroscopy experiments by linearly increasing the force from 0 µl/minutes to 2000 µl/minutes in 30 seconds. Rupture events observed in verified single tethered trajectories were analyzed in terms of the flow velocity and step height (ΔL) (FIG. 2B). The molecular loop-opening signature of the DNA construct was demonstrated as a powerful filtering parameter for specific DNA zipping [7]. The step height-filtered data in FIG. 2C reports the most probable flow rate in the event of rupture of 810 µl/min, providing a calibration factor for the FCI.

Dig—Anti-Dig Interaction

To verify the calibration and demonstrate the massive multiplexing capability of the FCI, dynamic force spectroscopy experiments were performed to determine the rupture force of the interaction between digoxigenin (Dig) and its antibody. The Dig—anti-Dig interaction was chosen because its energy landscape has been intensively studied [8, 9]. The digoxigenin group was coupled to one end of the DNA construct and the antibody was physiosorbed at the surface. Prior to force spectroscopy, a reverse flow experiment was performed to discriminate single-tethered beads using the filtering procedure described in the method section data analysis. After filtering, about 150 verified single-tethered beads per field of view were obtained, providing sufficient statistics for a force-histogram. It was determined that the most probable rupture force as a mean value of three independent experiments of 20.2 pN±3.2 pN for a loading rate of 5.4 pN/s (data not shown). The rupture force value is in good agreement with previous studies at similar loading rates [8].

To demonstrate the high capture efficiency of this approach, the surface coverage of nanoswitches was studied at different concentrations in solution. It was found that the number of verified single tethered beads increases linearly with increasing sample volume (data not shown). For example, when using a sample volume of 300 uL, a limit of detection of 1.4 aM was achieved. In other words, one molecule out of 180 target molecules in 300 ul can be captured.

Biomarker Detection

To demonstrate biomarker detection, human prostate specific antigen (PSA) was chosen as analyte. PSA is one of the most established biomarkers for screening, diagnosis and prognosis in the field of oncology [10] and is often used for demonstration in detection methods. For PSA detection, two different monoclonal PSA-antibodies were covalently coupled to DNA oligos in a one-step process using copper-free click chemistry. Subsequently, the oligos were hybridized onto the DNA construct. In case of a binding event with the target molecule PSA, the nanoswitches perform a conformation change from an "open" state to a "closed" state.

To characterize the molecular signatures of open and closed NS, the tether extension was examined at different pulling forces and included in the histogram in FIG. 3A. The histograms recorded at different pulling forces exhibit two peaks as expected for a heterogeneous mixture of open and closed tethers. The peaks shift to higher extension values for higher pulling forces, following the Worm Like Chain (WLC) model for a polymer with a persistence length of 48 nm (Baumann et al. 1997, ref. 23, Halvorsen et al. 2011, ref. 7) and a contour length of 2.58 μm±0.1 μm and 1.85 μm±0.1 μm, respectively. The contour length of 2.58 μm±0.1 μm is in good agreement with the expected length of the open NS containing 7308 base pairs when considering a contour length for each base pair of 0.34 nm. The contour length of the shorter tether is slightly larger than the expected contour length for the NS with a 2617 bp loop of 1.6 μm. The slightly larger contour length of several tenth of nanometer may be due to the additional length of the antibody-antigen complex inducing the conformation change.

Before sensing applications, the mechanical properties of the nanoswitches were characterized without PSA. Additional to the peak at a tether length of 2.58 μm, the histogram exhibits a small number of counts at different length and, also, at the length of the expected extension of a looped tether. Detection events in the absence of analyte are referred to as "false positive counts" and are caused by unspecific adhesive interaction, e.g. hydrophobic, electrostatic or van der Waals forces, arising between the antibodies coupled to the nanoswitch or between the antibodies and the DNA strand. These nonspecific interactions were found to be weak and decrease with increasing pulling force (see FIG. 3B). For high pulling forces above 12 pN, the number of observed tethers decreases significantly (see inset in FIG. 3B) due to the force-dependent off-rate of the digoxigenin-antibody complex (Neuert et al. [8]). All detection experiments in this study were carried out at a force of 6.5 pN, the optimum of high number of tethers and low false positive rate, if not stated differently.

The results obtained with the FCI were compared to the recently developed NLISA technique (Hansen et al.) [13], a gel shift assay where the slower migration of the closed nanoswitches causes a separation between open and closed NS (FIG. 3C). The intensity of the band of closed nanoswitches decreases with decreasing the concentration of PSA, indicating the specificity of the antibody-antigen recognition. The intensity of the bands in the gel shift assay is related to the number of DNA constructs contributing to the band. The relation between closed and open NS is within error of the values obtained with the force-controlled immunoassay indicating the remarkable compliance of both methods. However, the results obtained by NLISA refer to the average over thousands or billions of nanoswitches and, thus, are limited in sensitivity. In contrast, with FCI, single nanoswitches are probed individually enabling single-molecular resolution.

Biomarker Detection in Buffer and Serum

For ultra-sensitive biomarker detection, the sample is mixed with Anti-PSA functionalized nanoswitches in final concentrations of 150 pM to 1.5 nM. The high concentration of DNA origami constructs compared to the concentration of analyte accelerates the binding process and enables the detection of low analyte concentrations. However, the large number of open nanoswitches may block the binding sides on the surface, outnumbering the looped constructs. To single out the looped nanoswitches, restriction enzymes were used for DNA cleavage within the looped region. For isolating the looped constructs, the NS were tethered to magnetics beads and the cut DNA strands were washed out in several washing cycles (see FIG. 1F).

Typical histograms for different biomarker concentrations obtained with FCI are presented in FIG. 4A. A clear peak at 1.5 mm indicates the successful detection of PSA for concentrations as low as 8 aM for a sample volume of 100 ul. The second peak in the histogram in FIG. 4A at a tether length of about 2.5 μm indicates that not all nanoswitches are cleaved but some open nanoswitches remain. The number of closed NS was normalized on the total number of observed NS and plotted as a function of PSA concentration in FIG. 4B. The sample incubation with NS was performed in two different ways. For detecting biomarker concentrations above 10 fM, the sample was incubated with a final concentration of 1.5 nM NS for 90 minutes. For lower biomarker concentrations, the sample was incubated with a lower nanoswitch concentration of 150 pM for 12 hours. The lower nanoswitch concentration leads to a lower density of open nanoswitches at the surface and, thus, increases the detection sensitivity of the invention to an extrapolated LOD of 1.2 aM PSA in buffer, equivalent to 0.07 fg/ml.

To demonstrate biomarker detection in complex bodily fluids, human PSA was spiked into 50 ul 20% bovine serum sample (FIG. 4C). Dilution of serum samples is commonly used in immunoassays for reducing matrix effects caused by the high variance in the molecular composition of complex bodily fluids. An LOD of 138 aM was achieved in diluted serum samples corresponding to a LOD of 690 aM in 10 ul undiluted serum. This enables the detection of PSA in serum samples over five orders of magnitudes ranging from sub-femtomolar to picomolar levels. The lowest concentration tested in the assay was 500 aM (~15 fg/ml) in 20% serum. The high sensitivity of the assay is comparable with the most sensitive immunoassay reported by Rissin et al. of 1 fM in undiluted serum sample by using digital ELISA. To achieve such a high sensitivity, the incubation was performed for 90 minutes with a final concentration of 1.5 nM DNA nanoswitches. To prevent DNA degradation in serum, EDTA was added to the serum sample in a final concentration of 100 mM. After incubation, the looped constructs were singled out by using DNA cleavage enzymes. The total assay time was ~3 hours including incubation and optical read-out.

Biomarker Detection in Whole Blood

Biomarker detection in whole blood is particularly challenging because of its high diversity of biomolecules and their potential unspecific binding to the antibodies or DNA. The unspecific binding leads to an increased background signal in detection experiments compared to buffer or serum. This challenge was met by performing single-molecule force spectroscopy experiments after isolation of closed NS as described for serum. The design of the flow cell allows multiplexed force-spectroscopy experiments without the need of any technical changes on the instrument. Instead of using constant flow as in previous detection experiments, the flow and, thus, the force is ramped linearly and the bead movement is monitored. For statistical evaluation, between 400 and 1000 force-extension curves in each experiment were analyzed for rupture events. The rupture forces were summarized in histograms as shown in FIG. 5A. The force-histogram exhibits two peaks, one at a force of (6.3±0.39) pN and a second peak at a higher force of (9.7±1.7) pN. The first peak is in good agreement with the unspecific forces obtained from reverse flow experiments in section molecular signatures. The second peak is specific for experiments with PSA and refers to the rupture of the antibody-antigen complex.

For detection, the number of rupture events under the second peak is counted. To exclude nonspecific contributions, a lower cut-off value of 7.4 pN was set, corresponding to the most probable rupture force of nonspecific contributions plus three times the standard deviation. The specific rupture events were normalized on the total number of detected rupture events and included into the dose-response curve in FIG. 5B. The measurement was repeated for different PSA concentration and the control sample without any PSA. With this approach, a detection limit of 13 fM in whole blood was achieved. The high sensitivity is due to the low background signal caused by the force-controlled read-out. The antibody-antigen complex consists of two different antibodies bind to different regions of one antigen forming two bonds in series. The most probable rupture force is unique for this complex and is probably determined by the weaker of both antibodies with a nominal dissociation constant of 100 pM. There is evidence that the rupture force scales with the dissociation constant of an antibody-antigen complex [11]. Due to its lower dissociation constant of 10 pM, the second antibody is considered stronger and expected to sustain higher forces.

Discussion

As shown herein, the unique combination of DNA nanoswitches and a standard microfluidic channel enables the detection of prostate specific antigen (PSA) in biological fluids up to attomolar levels. This by far is the lowest limit of biomarker detection reported for single-molecule force experiments. The higher sensitivity compared to most standard detection assays is caused by a two-step approach combining the advantage of solution based immunoassay and a surface based read-out. In the initial step, the immunorecognition of antibody labeled DNA and biomarker is done in solution increasing the binding kinetics and avoiding surface-based effects. During incubation, the nanoswitches are present in a high concentration of several hundreds of picomolar to nanomolar, much higher than the dissociation constant of the antibodies (<10 pM). Two antibodies are required to obtain a positive detection signal. Both antibodies are coupled to the same DNA strand so that only one binding event per DNA strand is required. The local concentration of the antibodies on the DNA strand is about 15 nM, much higher than the dissociation constant of the weaker antibody (100 pM) resulting in a constant rebinding of the complex.

Prior to optical read-out, the nanoswitches sandwiching the analyte, referred to as the "on"-signal, are singled out using DNA cleavage enzymes for eliminating the linear nanoswitches. As being advantageous over other methods, the successful elimination of the "off"-signal enables the detection of very low concentrations in large volumes up to several 100 μl. To obtain single-molecule resolution, the DNA probes are tethered to a surface for optical read-out without the need of additional labeling. By counting the trajectories with the expected length, a detection limit of 1.2 aM was achieved in PBS buffer and a detection limit of 138 aM was achieved in 20% bovine serum. Due to the surface attachment of the nanoswitches, the false positive counts arising from nonspecific adhesive molecular interactions can be quantified and reduced. To our knowledge, this is the first disclosure of quantification of force dependent false positive rates for biomarker detection techniques. Suppressing false positive counts is of exceptional interest when working with complex bodily fluids. Complex bodily fluids such as blood contain a large variety of different proteins and can lead to large background signals. By using the rupture force as the characteristic parameter for detection, a LOD of 13 fM was achieved for PSA spiked into 10 μl whole blood diluted by 50%. The most probable rupture force of the antigen-antibody complex of (9.7±1.7) pN is revealed in force-ramping experiments. Due to the single-molecule resolution of the approach, the rupture force of up to 177 single PSA-antibody complexes was obtained in a single measurement of 20 seconds. To switch between reverse-flow and force-ramping experiments, no change in instrumentation is required.

In conclusion, a novel approach for attomolar biomarker detection with single molecule resolution has been presented herein. This approach is applicable for real detection measurements in complex bodily fluids such as diluted serum with a detection limit of 138 aM. The high sensitivity is caused by a force-controlled read-out with low background signal. As advantageous above other techniques, rapid massive parallel single-molecule force studies further decrease the background enabling a detection limit of 13 fM for whole blood. The demonstrated multiplexed single-molecule force assay is easy to perform for non-specialists and does not require any specific instrumentation or training. The force range in the dynamic mode is biologically relevant and suitable to measure the force-dependent binding strength of an antibody-antigen complex with single-molecule resolution in less than a minute. Due to its low costs, easy handling and rapid measurements, this technique may become a new standard for sensitive detection applications with low background signal. Beyond detection, the dynamic mode can be used for multiplexed single-molecule force spectroscopy studies and offer a new approach for rapid, low-cost screening in medical applications.

REFERENCES

[1] Puchner E M and Gaub H E 2012 Single-molecule mechanoenzymatics *Annual review of biophysics* 41 497-518.

[2] Keller D and Bustamante C 2000 The Mechanochemistry of Molecular Motors *Biophysical Journal* 78 541-56.

[3] Koirala D, Shrestha P, Emura T, Hidaka K, Mandal S, Endo M, Sugiyama H and Mao H 2014 Single-Molecule Mechanochemical Sensing Using DNA Origami Nanostructures *Angew. Chem.* 126 8275-9.

[4] Neuman K C and Nagy A 2008 Single-molecule force spectroscopy: optical tweezers, magnetic tweezers and atomic force microscopy *Nature methods* 5 491-505.

[5] Ke Y, Lindsay S, Chang Y, Liu Y and Yan H 2008 Self-assembled water-soluble nucleic acid probe tiles for label-free RNA hybridization assays Science (New York, N.Y.) 319 180-3.

[6] Yang D, Ward A, Halvorsen K and Wong W P 2016 Multiplexed single-molecule force spectroscopy using a centrifuge *Nature communications* 7 11026.

[7] Halvorsen K, Schaak D and Wong W P 2011 Nanoengineering a single-molecule mechanical switch using DNA self-assembly *Nanotechnology* 22 494005.

[8] Neuert G, Albrecht C, Pamir E and Gaub H E 2006 Dynamic force spectroscopy of the digoxigenin-antibody complex *FEBS letters* 580 505-9.

[9] Sitters G, Kamsma D, Thalhammer G, Ritsch-Marte M, Peterman E J G and Wuite G J L 2015 Acoustic force spectroscopy *Nature methods* 12 47-50.

[10] Lilja H, Ulmert D and Vickers A J 2008 Prostate-specific antigen and prostate cancer: prediction, detection and monitoring *Nature reviews. Cancer* 8 268-78.

[11] Schwesinger F, Ros R, Strunz T, Anselmetti D, Guntherodt H-J, Honegger A, Jermutus L, Tiefenauer L and Pluckthun A 2000 Unbinding forces of single antibody-antigen complexes correlate with their thermal dissociation rates Proceedings of the National *Academy of Sciences* 97 9972-7.

[12] Koussa, M. A., Halvorsen, K., Ward, A. and Wong, W. P., 2015. DNA nanoswitches: a quantitative platform for gel-based biomolecular interaction analysis. *Nature methods*, 12(2), pp. 123-126.

[13] C. H. Hansen, D. Yang, M. A. Koussa, W. P. Wong, Nanoswitch-linked immunosorbent assay (NLISA) for fast, sensitive, and specific protein detection, *Proc. Natl. Acad. Sci.* 114, 10367 (2017).

[14] I. F. Sbalzarini and P. Koumoutsakos, J. Struc. Biol., 151(2): 182-195, 2005

[15] C. A. Borrebaeck. Precision diagnostics: moving towards protein biomarker signatures of clinical utility in cancer. Nature Reviews Cancer 17, 199 (2017).

[16] C. Cabrera, L. Chang, M. Stone, M. Busch, D. H. Wilson. Rapid, fully automated digital immunoassay for p24 protein with the sensitivity of nucleic acid amplification for detecting acute HIV infection. Clinical chemistry 61, 1372 (2015).

[17] D. M. Rissin, C. W. Kan, T. G. Campbell, S. C. Howes, D. R. Fournier, L. Song, . . . , D. R. Walt, D. C. Duffy. Single-molecule enzyme-linked immunosorbent assay detects serum proteins at subfemtomolar concentrations. Nature biotechnology 28, 595 (2010).

[18] D. Yang, W. P. Wong, Repurposing a benchtop centrifuge for high-throughput single-molecule force spectroscopy, Methods in Molecular Biology: Single Molecule Analysis, 1665 (2018).

[19] T. Fazio, M. L. Visnapuu, S. Wind, E. C. Greene. DNA curtains and nanoscale curtain rods: high-throughput tools for single molecule imaging. Langmuir 24, 10524 (2008).

[20] I. F. Gallardo, P. Pasupathy, M. Brown, C. M. Manhart, D. P. Neikirk, E. Alani, I. Finkelstein. High-throughput universal DNA curtain arrays for single-molecule fluorescence imaging. Langmuir 31, 10310 (2015).

[21] A. R. Chandrasekaran, J. Zavala, K. Halvorsen. Programmable DNA nanoswitches for detection of nucleic acid sequences, ACS Sensors 1, 120 (2016).

[22] J. Silver, Z. Li Z, K. Neuman Tethered-bead, immune sandwich assay. Biosensors and Bioelectronics 63, 117-123 (2015).

[23] Baumann C G, Smith S B, Bloomfield V A and Bustamante C 1997 Ionic effects on the elasticity of single DNA molecules Proceedings of the National Academy of Sciences 94 6185-90.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

wherein the nanoswitch is a nucleic acid conjugated to a first and a second analyte-binding agent which when bound to the analyte adopts a looped conformation and a shorter length as compared to the length of the nanoswitch when it is not bound to the analyte, and wherein the closed nanoswitches are enriched and isolated by
(i) cleaving open and closed nanoswitches present after (a) with one or more endonucleases between the first and second analyte-binding agents,
(ii) end-conjugating the cleaved nanoswitches with a particle,
(iii) isolating the particle-conjugated nanoswitches, and
(iv) binding the particle-conjugated nanoswitches to a surface.

2. The method of claim 1, wherein the method measures length of the surface-tethered closed nanoswitch.

3. The method of claim 2, wherein the length of the surface-tethered closed nanoswitch is measured under constant force.

4. The method of claim 1, wherein the method detects a rupture event in the surface-tethered closed nanoswitch.

5. The method of claim 4, wherein the rupture event is detected under dynamic force.

6. The method of claim 1, wherein the method detects a plurality of rupture events in the same surface tethered closed nanoswitch under dynamic force, and the method then identifies the force at which the maximum number of rupture events occur.

7. The method of claim 1, wherein the one or more endonucleases is two endonucleases.

8. The method of claim 1, wherein the particle is a magnetic particle.

9. The method of claim 1, wherein the particle is a fluorescent particle.

10. The method of claim 1, wherein the particle is a quantum dot.

What is claimed is:

1. A method for detecting an analyte in a sample comprising
   (a) contacting a sample with a plurality of nanoswitches for a time and under conditions sufficient for binding of an analyte to the nanoswitch,
   (b) enriching and isolating closed nanoswitches bound to the analyte,
   (c) tethering the closed nanoswitches to a surface, and
   (d) measuring length of a single surface-tethered closed nanoswitch and/or detecting a rupture event in a single surface-tethered closed nanoswitch, under force, 11. The method of claim 1, wherein the nanoswitch is labeled with detectable stain or dye.

12. The method of claim 1, wherein the analyte-binding agents are antibodies or antigen-binding antibody fragments.

13. A method for detecting an analyte in a sample comprising
   (a) contacting a sample with a plurality of nanoswitches each end-conjugated to a bead for a time and under conditions sufficient for binding of an analyte to a nanoswitch thereby forming a mixture of closed and open nanoswitches,
   (b) tethering closed and open nanoswitches to a surface, (c) identifying surface-tethered closed nanoswitches having symmetrical trajectories under forward and reverse forces, and (d) measuring length of single surface-tethered closed nanoswitches and/or detecting rupture event of single surface-tethered closed nanoswitch, under force, wherein the nanoswitch is a nucleic acid conjugated to a first and a second analyte-binding agent which when bound to the analyte adopts a looped conformation and a shorter length as compared to the length of the nanoswitch when it is not bound to the analyte.

14. The method of claim 13, further comprising, between steps (a) and (b), enriching and isolating closed nanoswitches bound to the analyte.

15. A method for detecting an analyte in a sample comprising (a) contacting a sample with a plurality of nanoswitches, each nanoswitch conjugated at a first end to a lipid and at a second end to a particle, for a time and under conditions sufficient for binding of an analyte to a nanoswitch, thereby forming a mixture of closed and open nanoswitches, (b) aligning and extending the closed and open nanoswitches in a fluid lipid bilayer using force, and (c) identifying, and optionally measuring, closed nanoswitches based on length, wherein the nanoswitch is a nucleic acid conjugated to a first and a second analyte-binding agent which when bound to the analyte adopts a looped conformation and has a shorter length as compared to the length of the nanoswitch when it is not bound to the analyte.

16. The method of claim 15, wherein the nanoswitches of (a) are in solution, and after the time sufficient for binding to an analyte are inserted into the lipid bilayer.

17. The method of claim 15, wherein the nanoswitches are labeled with a detectable stain or dye.

18. A method for detecting an analyte in a sample comprising (a) providing a surface-tethered complex, wherein the complex comprises an analyte bound to a first and a second analyte binding agent, wherein the first analyte-binding agent is coupled to a bead and the second analyte-binding agent is coupled to a surface, (b) applying a force to the complex, and optionally identifying surface-tethered complexes having symmetrical trajectories under forward and reverse forces, (c) measuring, for individual surface-tethered complexes, length of the complex under force, and/or the force required to rupture the bead from the second analyte-binding agent under dynamic force, and/or lifetime of the complex under constant force.

19. The method of claim 18, wherein the first analyte-binding agent is coupled to the bead with a nucleic acid.

20. The method of claim 18, wherein the second analyte-binding agent is coupled to the surface with a nucleic acid.

* * * * *